US008415506B2

(12) United States Patent
Waibel et al.

(10) Patent No.: US 8,415,506 B2
(45) Date of Patent: Apr. 9, 2013

(54) ENERGY EFFICIENT ACETONE DRYING METHOD

(75) Inventors: Brian J. Waibel, Kenneth Square, PA (US); Hans Schonemann, Newburyport, MA (US); David J. Lawrence, Newark, DE (US); Paul Robinson, Newark, DE (US)

(73) Assignee: DynaSep Inc., Wilmington, DE (US)

( * ) Notice: Subject to any disclaimer, the term of this patent is extended or adjusted under 35 U.S.C. 154(b) by 127 days.

(21) Appl. No.: 12/944,030

(22) Filed: Nov. 11, 2010

(65) Prior Publication Data

US 2011/0112329 A1 May 12, 2011

Related U.S. Application Data

(60) Provisional application No. 61/260,245, filed on Nov. 11, 2009.

(51) Int. Cl.
*C07C 45/80* (2006.01)
*B01D 11/04* (2006.01)

(52) U.S. Cl. ........................................ 568/411; 210/634
(58) Field of Classification Search .................. 568/411; 210/511, 634
See application file for complete search history.

(56) References Cited

U.S. PATENT DOCUMENTS

| | | | |
|---|---|---|---|
| 3,969,196 A | 7/1976 | Zosel | |
| 4,280,961 A | 7/1981 | Schneider et al. | |
| 4,339,882 A | 7/1982 | Dickey et al. | |
| 4,459,762 A | 7/1984 | Hardesty et al. | |
| 4,613,429 A | 9/1986 | Chiang | |
| 4,749,522 A | 6/1988 | Kamarei | |
| 4,877,530 A * | 10/1989 | Moses | 210/511 |
| 4,964,995 A | 10/1990 | Chum et al. | |
| 5,287,632 A | 2/1994 | Heit et al. | |
| 5,312,549 A | 5/1994 | String | |
| 5,364,475 A | 11/1994 | Levien et al. | |
| 6,037,492 A | 3/2000 | Lopez de Hierro | |
| 6,326,504 B1 | 12/2001 | Piquer | |
| 6,700,014 B2 | 3/2004 | Jerz | |
| 6,800,299 B1 | 10/2004 | Beaudoin et al. | |
| 2006/0116463 A1 | 6/2006 | Erkey | |
| 2007/0098808 A1 | 5/2007 | Sampalis | |

FOREIGN PATENT DOCUMENTS

| | | |
|---|---|---|
| CN | 1228432 A | 9/1999 |
| WO | 2008147705 | 12/2008 |
| WO | WO/2011/060170 | 5/2011 |

OTHER PUBLICATIONS

Emitech, 'Critical Point Drying Incorporating Emitech K850.' Technical Brief, Emitech Ltd., Mar. 18, 1999, p. 4, 5 [online] downloaded from URL <http://www.chm.bris.ac.uklemuweb/CriticaiPointDryer.pdf>.
Panagiotopoulos et al., 'High-pressure Phase Equilibria in Ternary Fluid Mixtures with a Supercritical Component' Department of Chemical Engineering, Massachusetts Institute of Technology, Cambridge, MA, Sep. 1985, entire document [online] downloaded from URL <http://www.anl.goy/PCS/acsfuellpreprint%20archive/Files/30_3_CHICAGO_09-85_0046.pdf>.
PCT International Search Report for Application No. PCT/US2010/56382, issued Feb. 2, 2011, 1 page total.
Ennis et al., (1986) "Continuous Product Recovery by In-Situ Gas Stripping/Condensation During Solvent Production From Whey Permeate Using *Clostridium acetobutylicum*", *Biotechnology Letters* 8(10):725-730.
Laitinen et al., (1999) "Supercritical fluid extraction of 1-butanol from acqueous solutions", *Journal of Supercritical Fluids* 15:245-252.
Maddox et al. (1995) "Production of Acetone-Butanol-Ethanol from Concentrated Substrates Using *Clostridium acetobutylicum* in an Integrated Fermentation-Product Removal Process", *Process Biochemistry* 30(3)209-215.
Panagiotopoulos et al. (1986) "Multiphase High Pressure Equilibria in Ternary Aqueous Systems", *Fluid Phase Equilibria* 29:525-534.
Qureshi et al. (2001) "Recovery of butanol from fermentation broth by gas stripping", *Renewable Energy* 22:557-564.
International Preliminary Report on Patentability and Written Opinion dated May 15, 2012 issued in PCT/US2010/056382 (WO/2011/060170).
Optima Chemical Group, LLC (2013) "Biomass Extraction" pp. 1-2 [retrieved on Jan. 30, 2013]. Retrieved from the Internet: http://www.optimachem.com/biomass.htm.
Phasex Corporation (2013) "Nutraceuticals and Supercritical Fluid Applications" pp. 1-5 [retrieved on Jan. 30, 2013]. Retrieved from the Internet: http://phasex4scf.com/supercritical_markets/supercritical_fluids_nutraceuticals.htm.

* cited by examiner

*Primary Examiner* — Sikarl Witherspoon
(74) *Attorney, Agent, or Firm* — Jennifer L. Wahlsten; Weaver Austin Villeneuve & Sampson LLP

(57) ABSTRACT

The present invention provides energy and economically efficient and environmentally responsible processes for using acetone to dry, dehydrate and/or dewater various hydrated feedstocks.

43 Claims, 12 Drawing Sheets

ENERGY EFFICIENT ACETONE DRYING METHOD

CROSS-REFERENCE TO RELATED APPLICATIONS

The present application claims the benefit of U.S. Provisional Application No. 61/260,245, filed on Nov. 11, 2009, the entire contents of which is hereby incorporated herein by reference for all purposes.

FIELD OF THE INVENTION

The present invention provides energy and economically efficient and environmentally responsible processes for using acetone to dry, dehydrate and/or dewater various feedstock.

BACKGROUND OF THE INVENTION

Acetone is both miscible with water and can be used to displace water. Due to its high vapor pressure, the evaporation of acetone is useful for removing the residual water in a feedstock, e.g., a biomaterial, geologic or carbonaceous material, waste-water. Similarly, acetone is used to facilitate drying of glassware in chemistry, biochemistry, and biotechnology laboratories.

Acetone drying is used at laboratory scale due to the rapid action of the acetone and the insignificant cost of due to loss of acetone. Acetone drying techniques, as applied in a chemistry laboratory setting, have not been used at large scale due to the prohibitively large volatile organic compound emissions, consequent environmental concerns and costs associated with acetone loss.

Thermal drying techniques have been preferred over acetone drying techniques. This is because the most conventional embodiment of an acetone drying method at commercial scale would require distillation to separate the acetone from the water. The capital and operating expenses of such a facility are higher than those for a conventional spray drying and drum drying, two of the most-efficient methods for thermal drying materials. Because of the lack of operational expense advantage, solvent drying with acetone has not been employed at large scale.

BRIEF SUMMARY OF THE INVENTION

The present invention provides energy efficient processes for drying hydrated feedstock using acetone. The processes can be performed at ambient temperature and without requiring distillation. The processes allow for the economically viable and environmentally responsible use of large volumes of acetone for dehydration or dewatering of various hydrated feedstock sources, including without limitation biological matter, hydrocarbon-laden matter, geologic matter, and wastewater streams.

Accordingly, in one aspect, the invention provides processes of recovering acetone from an aqueous solution. In some embodiments, the process comprises.

a) contacting an aqueous solution comprising at least about 40 wt % water and at least about 30 wt % acetone with carbon dioxide in an amount that is about 10-50 wt/wt % of the aqueous solution and at a pressure that is about 0.2 to about 10 times the vapor pressure or critical pressure of the carbon dioxide, wherein the carbon dioxide disrupts the aqueous solution into a biphasic mixture comprising an acetone-rich phase and a water-rich phase; and b) non-thermally separating the acetone-rich phase from the water-rich phase, thereby recovering substantially all the acetone from the aqueous solution. In some embodiments, at least about 85%, 90%. 95%, 96%, 97%, 98%, or 99% of the acetone is recovered.

In another aspect, the invention provides drying or dewatering hydrated feedstock at ambient temperature. In some embodiments, the processes comprise the following ordered steps of:

a) contacting the hydrated feedstock comprising water and insoluble solid with acetone, thereby yielding a first slurry comprised of at least about 30% acetone, water and the insoluble solid, wherein the acetone extracts the water from the insoluble solid;

b) extracting the acetone and water from the insoluble solid by contacting with liquid phase carbon dioxide; thereby yielding a second slurry comprised of carbon dioxide, acetone, water and the insoluble solid, wherein the carbon dioxide displaces the water and acetone in the insoluble solid;

c) separating the insoluble solid from the second slurry; thereby yielding insoluble solid saturated with liquid phase carbon dioxide and a solution comprising liquid phase carbon dioxide, acetone and water; and d) depressurizing the insoluble solid to atmospheric pressure to release gas phase carbon dioxide, thereby yielding dried or dewatered insoluble solid.

In some embodiments, the process further comprises step a2) before step b) of concentrating the first slurry, thereby yielding a concentrated slurry comprising a higher mass fraction of insoluble solid, acetone and water. The concentrated slurry can be separated from the superfluous aqueous solution comprising acetone and water, e.g., the filtrate. In some embodiments, the slurry is concentrated by filtration.

In some embodiments, steps a) and a2) are repeated two or more times, for example, 2, 3, 4, 5 or more times. In some embodiments, steps b) and c) are repeated two or more times, for example, 2, 3, 4, 5 or more times.

In some embodiments, the first slurry comprises at least about 30%, 35%, 40%, 45%, 50% acetone.

In some embodiments, the process further comprises the step of recovering the acetone from the aqueous solutions in the first and/or second slurries. In some embodiments, acetone is recovered from the aqueous solution of the first slurry comprising acetone and water. In some embodiments, acetone is recovered from the aqueous solution of the second slurry comprising acetone, water and carbon dioxide. In some embodiments, acetone is recovered from the aqueous solutions combined from the first and second slurries.

In some embodiments, the acetone is recovered by i) contacting the solution with vapor phase carbon dioxide, thereby splitting the solution into an upper (i.e., lower density) acetone-rich phase and a lower (i.e., higher density) water-rich phase; and ii) non-thermally separating the upper acetone-rich phase from the lower water-rich phase.

In some embodiments, the hydrated feedstock further comprises oil, and the acetone is recovered by i) separating the insoluble solid from the first slurry, thereby yielding a solution comprising acetone, water and oil;

ii) adding water to the solution comprising acetone, water and oil to form a biphasic mixture comprising an oil-rich phase and a water rich phase;

iii) contacting the oil-rich phase with liquid phase carbon dioxide, thereby stripping the acetone from the oil; and iv) contacting the water-rich phase with vapor phase carbon dioxide, thereby splitting the solution into an upper acetone-rich phase and a lower water-rich phase; and v) non-thermally separating the upper acetone-rich phase from the lower water-rich phase.

In some embodiments, the processes further comprise the step of recovering the gas phase carbon dioxide released from the solution in step d).

In a further aspect, the invention provides processes for acetone-drying hydrated feedstock at ambient temperature, comprising:

a) contacting the hydrated feedstock comprising water and insoluble solid with acetone, thereby yielding a first slurry comprised of acetone, water and the insoluble solid, wherein the acetone extracts the water from the insoluble solid;

b) separating the insoluble solid within the first slurry; thereby yielding insoluble solid saturated with acetone and a first solution comprising acetone and water; wherein the insoluble solid is dehydrated, and c) recovering the acetone from the solution of step b) comprising contacting the solution with vapor phase carbon dioxide, thereby splitting the solution into an acetone-rich phase and a water-rich phase and separating the acetone-rich phase from the water-rich phase; wherein the acetone is recovered.

In a related aspect, the invention provides processes for acetone-drying hydrated feedstock at ambient temperature, comprising:

a) contacting the hydrated feedstock comprising water, oil and insoluble solid with acetone, thereby yielding a first slurry comprised of acetone, water, oil and the insoluble solid, wherein the acetone extracts the water and oil from the insoluble solid;

b) separating the insoluble solid within the first slurry; thereby yielding insoluble solid saturated with acetone and a first solution comprising acetone, oil and water; wherein the insoluble solid is dehydrated, and c) recovering the acetone from the solution of step b) comprising adding water to the first solution comprising acetone, water and oil to form a biphasic mixture comprising an oil-rich phase and a first water-rich phase; and contacting the oil-rich phase with liquid phase carbon dioxide, thereby stripping the acetone from the oil; and contacting the first water-rich phase with vapor phase carbon dioxide, thereby splitting the solution into an acetone-rich phase and a second water-rich phase and separating the acetone-rich phase from the second water-rich phase; wherein the acetone is recovered.

In some embodiments, steps a) and b) are repeated two or more times, for example, 2, 3, 4, 5 or more times.

In some embodiments, the acetone-rich phase recovered in step c) is contacted with the hydrated feedstock in step a).

In some embodiments, the processes further comprise after step b) the steps of:

i) extracting the acetone and water from the insoluble solid by contacting with liquid phase carbon dioxide; thereby yielding a second slurry comprised of carbon dioxide, acetone, water and insoluble solid, wherein the carbon dioxide displaces the water and acetone in the insoluble solid;

ii) separating the insoluble solid from the second slurry; thereby yielding insoluble solid saturated with liquid phase carbon dioxide and a second solution comprising liquid phase carbon dioxide, acetone and water; and iii) depressurizing the insoluble solid saturated with liquid phase carbon dioxide to atmospheric pressure to release gas phase carbon dioxide, thereby yielding dehydrated insoluble solid.

In some embodiments, the hydrated feedstock comprises oil, wherein the acetone extracts the water and the oil from the insoluble solid, yielding a first solution comprising acetone, water and oil; and further comprising after step b) the step of non-thermally separating the acetone from the oil.

In some embodiments, the acetone is separated from the oil by adding water to the first solution comprising acetone, water and oil to form a biphasic mixture comprising an oil-rich phase and a water rich phase; and contacting the oil-rich phase with liquid phase carbon dioxide, thereby stripping the acetone from the oil; and contacting the water-rich phase with vapor phase carbon dioxide, thereby splitting the solution into an acetone-rich phase and a water-rich phase and separating the acetone-rich phase from the water-rich phase; wherein the acetone is recovered (as in step c)).

In some embodiments, steps i) and ii) are repeated two or more times, for example, 2, 3, 4, 5 or more times.

In some embodiments, the gas phase carbon dioxide released is captured and pressurized to liquid phase and contacted with the first slurry of step a).

In some embodiments, the first solution and the second solution are combined before performing step c).

In a related aspect, the invention provides for processes drying or dewatering hydrated feedstock at ambient temperature, comprising the following steps of:

a) contacting the hydrated feedstock comprising water and insoluble solid with acetone, thereby yielding a first slurry comprising insoluble solid and a first aqueous solution comprising acetone and water, wherein the acetone extracts the water from the insoluble solid, thereby yielding an insoluble solid saturated with acetone;

b) separating the insoluble solid saturated with acetone from the first aqueous solution;

c) extracting the acetone from the insoluble solid by contacting with liquid phase carbon dioxide; thereby yielding a second slurry comprised of the insoluble solid and a second aqueous solution comprising acetone, water and carbon dioxide, wherein the carbon dioxide displaces the water and acetone in the insoluble solid thereby yielding insoluble solid saturated with carbon dioxide;

d) separating the insoluble solid saturated with carbon dioxide from the second aqueous solution; and e) depressurizing the insoluble solid saturated with carbon dioxide to atmospheric pressure to release gas phase carbon dioxide, thereby yielding dried or dewatered insoluble solid;

f) recovering the acetone from the first and/or the second aqueous solutions by
 i) contacting the first and/or the second aqueous solutions with vapor phase carbon dioxide, thereby splitting the solution into an upper (i.e., lower density) acetone-rich phase and a lower (i.e., higher density) water-rich phase; and
 ii) separating the upper acetone-rich phase from the lower water-rich phase.

In a related aspect, the invention provides processes for drying or dewatering hydrated feedstock at ambient temperature, comprising the following steps of:

a) contacting the hydrated feedstock comprising oil, water and insoluble solid with acetone, thereby yielding a first slurry comprising insoluble solid and a first aqueous solution comprising acetone, oil and water, wherein the acetone extracts the oil and water from the insoluble solid, thereby yielding an insoluble solid saturated with acetone;

b) separating the insoluble solid saturated with acetone from the first aqueous solution;

c) extracting the acetone from the insoluble solid by contacting with liquid phase carbon dioxide; thereby yielding a second slurry comprised of the insoluble solid and a second aqueous solution comprising acetone, oil, water and carbon dioxide, wherein the carbon dioxide displaces the oil, water and acetone in the insoluble solid thereby yielding insoluble solid saturated with carbon dioxide;

d) separating the insoluble solid saturated with carbon dioxide from the second aqueous solution; and e) depressurizing the insoluble solid saturated with carbon dioxide to atmospheric pressure to release gas phase carbon dioxide, thereby yielding dried or dewatered insoluble solid;

f) recovering the acetone from the first and/or the second aqueous solutions by
  i) contacting the first and/or the second aqueous solutions with water, thereby forming a biphasic mixture comprising an oil-rich phase and a first water-rich phase;
  ii) contacting the oil-rich phase with liquid phase carbon dioxide, thereby stripping the acetone from the oil;
  iii) contacting the first water-rich phase with vapor phase carbon dioxide, thereby splitting the solution into an upper (i.e., lower density) acetone-rich phase and a lower (i.e., higher density) second water-rich phase; and
  iv) separating the upper acetone-rich phase from the lower second water-rich phase.

In some embodiments, steps a) and b) are repeated two or more times, for example, 2, 3, 4, 5 or more times. In some embodiments, steps c) and d) are repeated two or more times, for example, 2, 3, 4, 5 or more times.

With respect to further embodiments of the processes described herein, the processes can be performed continuously or in batches.

In some embodiments, the acetone-water aqueous solution comprises at least about 40, 45, 50, 55, 60, 65, 70 wt % water. In some embodiments, the acetone-water aqueous solution comprises at least about 30, 35, 40, 45, 50, 55, 60 wt % acetone.

In some embodiments, the process is performed at a pressure that is about 0.3 to about times, about 0.5 to about 2 times, or about 0.75 to about 1.25 times, the vapor pressure or critical pressure of the carbon dioxide. In some embodiments, the process is performed at a pressure that is below the vapor pressure of carbon dioxide. In some embodiments, the process is performed at a pressure that is about 0.5 to about 0.95 the vapor pressure of carbon dioxide.

In some embodiments, the process is performed below the critical temperature of carbon dioxide. In some embodiments, the process is performed below 31° C. In some embodiments, the process is performed at a temperature in the range of about 20-35° C., for example, about 25-30° C.

In some embodiments, the process is performed at a temperature below 31° C., and the pressure is from about 0.2 to about 10 times, for example, about 0.3 to about 5 times, about 0.5 to about 2 times, or about 0.75 to about 1.25 times, the vapor pressure of carbon dioxide.

In some embodiments, the process is carried out at a large or commercial scale. For example, the aqueous solution can comprise a volume of at least about 2 L, 5 L, 10 L, 25 L, 50 L, 75 L, 100 L, 500 L, 1000 L, 2000 L, 5000 L, 7500 L, 10,000 L, 20,000 L, 50,000 L, 100,000 L, or more, as needed or desired.

In some embodiments, the feedstock is first downsized to particles of about 500 μm or less. In some embodiments, the feedstock is first downsized to particles of about 25-500 μm.

In some embodiments, the process is performed at ambient temperature (i.e., without heating or cooling, e.g., of the hydrated feedstock). In some embodiments, the process is performed without distillation.

In some embodiments, the process is performed at a temperature above 31° C., and the pressure is from about 0.2 to about 10 times, for example, about 0.3 to about 5 times, about 0.5 to about 2 times, or about 0.75 to about 1.25 times, the critical pressure of carbon dioxide.

In some embodiments, the aqueous solution is contacted with the carbon dioxide in a countercurrent column. In some embodiments, the aqueous solution is contacted with the carbon dioxide in a vessel.

The acetone-rich phase can be separated from the water-rich phase using any method known in the art, preferably without the input of heat, e.g., for distillation. Generally, the acetone-dominated or acetone-rich phase is of a relatively lower density; the water-dominated or water-rich phase is of a relatively higher density. In some embodiments, the acetone-rich phase is separated non-thermally from the water-rich phase. In some embodiments, non-thermal separation includes, e.g., decantation, centrifuging, cyclonic separation, or membrane filtration.

In some embodiments, the process further comprises the step of removing carbon dioxide from the acetone-rich phase or the water-rich phase.

In some embodiments, the recovered acetone is re-used and contacted with hydrated feedstock.

In some embodiments, the recovered carbon dioxide is re-used and contacted with acetone saturated feedstock and/or an aqueous solution comprising acetone and water.

The feedstock can be from numerous sources, including without limitation biological matter, geological matter, hydrocarbon-laden matter, and wastewater streams.

In some embodiments, the hydrated feedstock is biological matter. For example, the biological matter can be without limitation, animal, fungal or plant matter, edible or non-edible. In some embodiments, the biological matter is a mass (e.g., a cake, a paste, a slurry) of single-celled organisms, e.g., a mass of yeast cells, bacterial cells or algae cells. In some embodiments the plant matter is selected from tuber vegetables (e.g., potatoes), root or family Apiaceae vegetables (e.g., carrots, parsnips, turnips, beets, fennel, celery, celeriac, etc), crucifers or brassica or family Brassicaceae vegetables (e.g., broccoli, cauliflower, cabbage, collards, rutabaga, brussels sprouts, radish, etc.), family Liliaceae vegetables (e.g., onions, garlic, leeks, shallots, chives, asparagus), nightshade or family Solanaceae vegetables (e.g., tomatoes, eggplant, capsicum peppers, etc.) and/or family Cucurbitaceae (e.g., cucumbers, watermelons, melons, squash, marrow, etc.). In some embodiments, the biological matter is a meat product (e.g., beef, veal, pork, mutton, lamb, poultry, fish, crustaceans, etc.).

In some embodiments, the hydrated feedstock is hydrocarbon-laden matter. In some embodiments, the hydrated feedstock is geological matter. In some embodiments, the hydrated feedstock is from a tar sands tailings pond.

In some embodiments, the hydrated feedstock is from a wastewater stream. In some embodiments, the hydrated feedstock is wastewater from a natural gas drilling site.

DEFINITIONS

The term "superambient pressure" refers to a pressure above the pressure at ambient conditions.

The term "subambient pressure" refers to a pressure below the pressure at ambient conditions.

The pressure at ambient conditions or "ambient pressure" exists without applied pressure or vacuum.

The term "superambient temperature" refers to a temperature above the temperature at ambient conditions.

The term "subambient temperature" refers to a temperature below the temperature at ambient conditions.

The temperature at ambient conditions or "ambient temperature" exists without applying heating or cooling.

The term "non-thermally" refers to a process or step performed without the input of heating or cooling.

The term "large scale" or "commercial scale" as used herein refers to processes performed at a volume of about 2 L or more. Large scale processes of the present invention may be carried out at volumes that are one or more orders of magnitude greater, for example, in some embodiments, the processes are carried out on the order of hundreds of liters, thousands of liters, tens of thousands of liters or hundreds of thousands of liters. In some embodiments, the processes of the present invention are carried out at a volume of at least about, e.g., 5 L, 10 L, 25 L, 50 L, 75 L, 100 L, 500 L, 1000 L, 2000 L, 5000 L, 7500 L, 10,000 L, 20,000 L, 50,000 L, 100,000 L, or more, as needed or desired.

The term "hydrated feedstock" refers to matter comprised of solid constituents that are insoluble in both water and acetone, and at least 20 wt % water. In some embodiments, the hydrated feedstock comprises at least about 20 wt %, 30 wt %, 40 wt %, 45 wt %, 50 wt %, 55 wt %, 60 wt %, 65 wt %, 70 wt %, 75 wt %, 80 wt %, 85 wt %, 90 wt %, 95 wt % water. Hydrated feedstock includes without limitation biological matter and geological matter. For example, algae feedstock may contain as much as about 95% water. Some vegetable feedstocks may contain at least about 80% water.

The term "insoluble solid" refers to the component of a hydrated feedstock or a slurry comprising a hydrated feedstock that are insoluble or have extremely low solubility in acetone and water, i.e., on the order of less than about 10 ppm. Insoluble solid may refer to a single particle or a collection of particles. Insoluble solids in biological matter includes, e.g., fiber, sugars, protein, and minerals. Fibers would be comprised of both water soluble and water insoluble fiber. Sugars include fructose, glucose, sucrose, maltose, and lactose. Minerals can be determined via the ash measurement in nutritional testing. Insoluble solids in geologic matter include, e.g., inorganic materials, including igneous, sedimentary, and metamorphic rock. This includes without limitation mudstone, shale, siltstone, sandstone, limestone, dolostone. In addition, insoluble material can refer to mineral salts including sodium chloride, calcium chloride, calcium carbonate. Minerals can include talc, gypsum, calcite, fluorite, apatite, orthoclase, quartz, topaz, corundum, and diamond.

The term "geological matter" or "terrestrial matter" interchangeably refer to solid, inanimate matter extracted from the earth. For the purposes of the present invention, the geological matter will contain extractable solute from natural and/or unnatural sources. Solute in geological matter from natural sources can include, for example, hydrocarbon substances, including tar, natural gas, crude oil, etc. Solute in geological matter from unnatural sources (i.e., waste) can include, for example, hydrocarbon substances, including tar, natural gas, crude oil, refined oil, industrial waste, synthesized organic compounds, etc. Exemplified geological matter suitable for extraction by the present methods and systems include, without limitation, oil cuttings, tar sands, oil shale, and the like.

The term "biological matter" refers to solid matter, viable or non-viable, from species of any of the biological kingdoms, including animal, plant, fungi, protista, eubacteria, and archaebacteria.

The term "plant matter" refers to solid matter, viable or non-viable, from species of the plant kingdom. Exemplified plant matter can be from any part of a plant, including, without limitation, seeds, stems, leaves, roots, flowers, fruits, vegetables, pollen, and the like.

The term "animal matter" refers to solid matter, viable or non-viable, from species of the animal kingdom. The animal matter will oftentimes be composed of proteins, bone and/or fats.

Animal matter "rendering" refers to any processing of animal byproducts into more useful materials, for example, the rendering of whole animal fatty tissue into purified fats like lard or tallow. Rendering material can include the fatty tissue, bones, and offal, as well as entire carcasses of animals. Animal matter sources include beef, pork, sheep, and poultry. The rendering process simultaneously dries the material and separates the fat from the bone and protein. In some cases, a rendering process yields a fat commodity (e.g., yellow grease, choice white grease, bleachable fancy tallow, etc.) and a protein meal (e.g., meat & bone meal, poultry byproduct meal, etc.).

The terms "extraction," "extracting" and "extracted" interchangeably refer to the process of drawing one component of a mixture into another mixture. In the present invention, the water is first drawn from the feedstock into the acetone, and then acetone is extracted into the carbon dioxide, away from the insoluble solid and the water.

The phrase "converting to vapor phase" refers to the step of altering the temperature and pressure of the carbon dioxide apparatus to change the phase of the carbon dioxide from liquid phase or near supercritical phase to the vapor phase.

The term "liquid phase" refers to carbon dioxide under the appropriate temperature and pressure conditions in order to form a liquid phase. Provided the temperature and pressure are below the critical point for carbon dioxide (30.978° C. and 73.773 bar), the liquid phase of carbon dioxide can be achieved through pressure alone, temperature alone, or through a combination of temperature and pressure. One of skill in the art will know what temperature and pressure are appropriate to form the liquid phase of carbon dioxide.

The term "supercritical phase" refers to carbon dioxide under the appropriate temperature and pressure conditions in order to form a supercritical phase or near supercritical phase. This exists at a temperature and pressure that exceeds the critical temperature of 30.978° C. and critical pressure of 73.773 bar. One of skill in the art will know what temperature and pressure are appropriate to form the supercritical phase of carbon dioxide.

The term "biphasic dense gas" refers to a gas maintained at a pressure and temperature condition such that gas can simultaneously exist in vapor and liquid phase. For the purposes of the present invention, the pressure and temperature of the dense gas is below the critical temperature and/or pressure of the gas. Because the gas exists in a biphasic state, either the pressure is maintained as the independent variable while the temperature is a dependent quantity or the temperature is maintained as the dependent variable while the pressure is a dependent quantity.

The term "recycle" refers to the processing of materials so that the materials can be used again. Following extraction of the acetone and vaporization, the carbon dioxide is condensed back to the liquid phase and returned to the step of acetone extraction with carbon dioxide. The recycling prevents resources from being wasted, reduces the consumption of raw materials and reduces energy usage.

The term "reuse" refers to the act of using for a subsequent time, an item that has already been used and discarded. In the present invention, the carbon dioxide used in the extraction is converted to the vapor phase in order to yield dehydrated or dewatered feedstock. The vapor phase carbon dioxide is recycled via condensation and supplied back to the extraction process, thus being used again to extract additional acetone from the feedstock and acetone-water solution.

The phrase "continuous" or "continuous flow" process refers to a process having constant input and output. A continuous flow process is in contrast to a process that requires batch or discontinuous processing.

The term "substantially," e.g., with regard to recovery or dehydration, refers to at least 80% recovery or dehydration, e.g., at least about 85%, 90%. 95%, 96%, 97%, 98%, 99% recovery or dehydration.

DETAILED DESCRIPTION

1) Introduction

Figure 1:
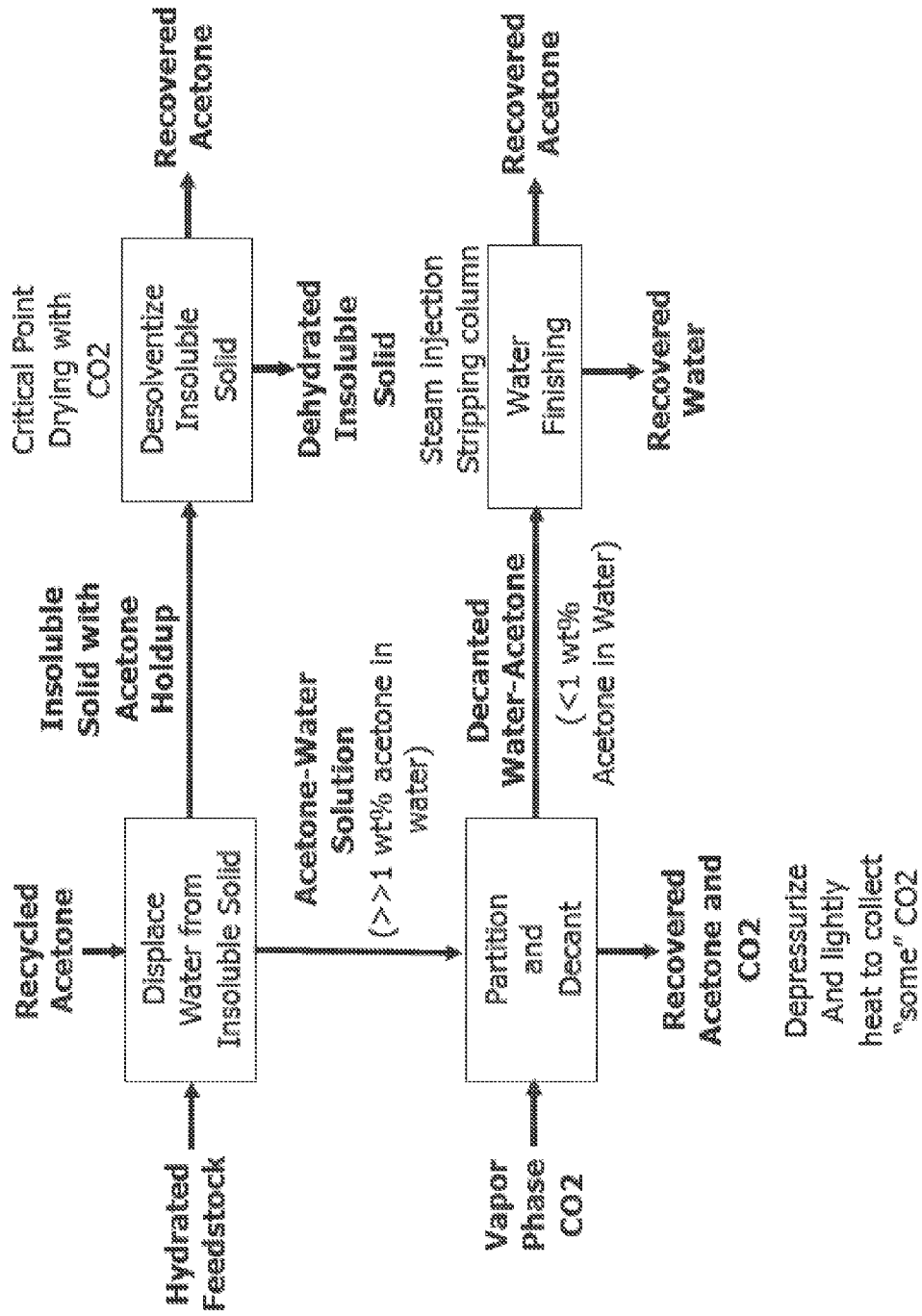
FIG. 1 illustrates the four major process operations of the present drying process:
  a) Displacement of Water from Insoluble Solid
  b) Desolventize Insoluble Solid
  c) Partition and Decant
  d) Water Finishing
Figure 2:
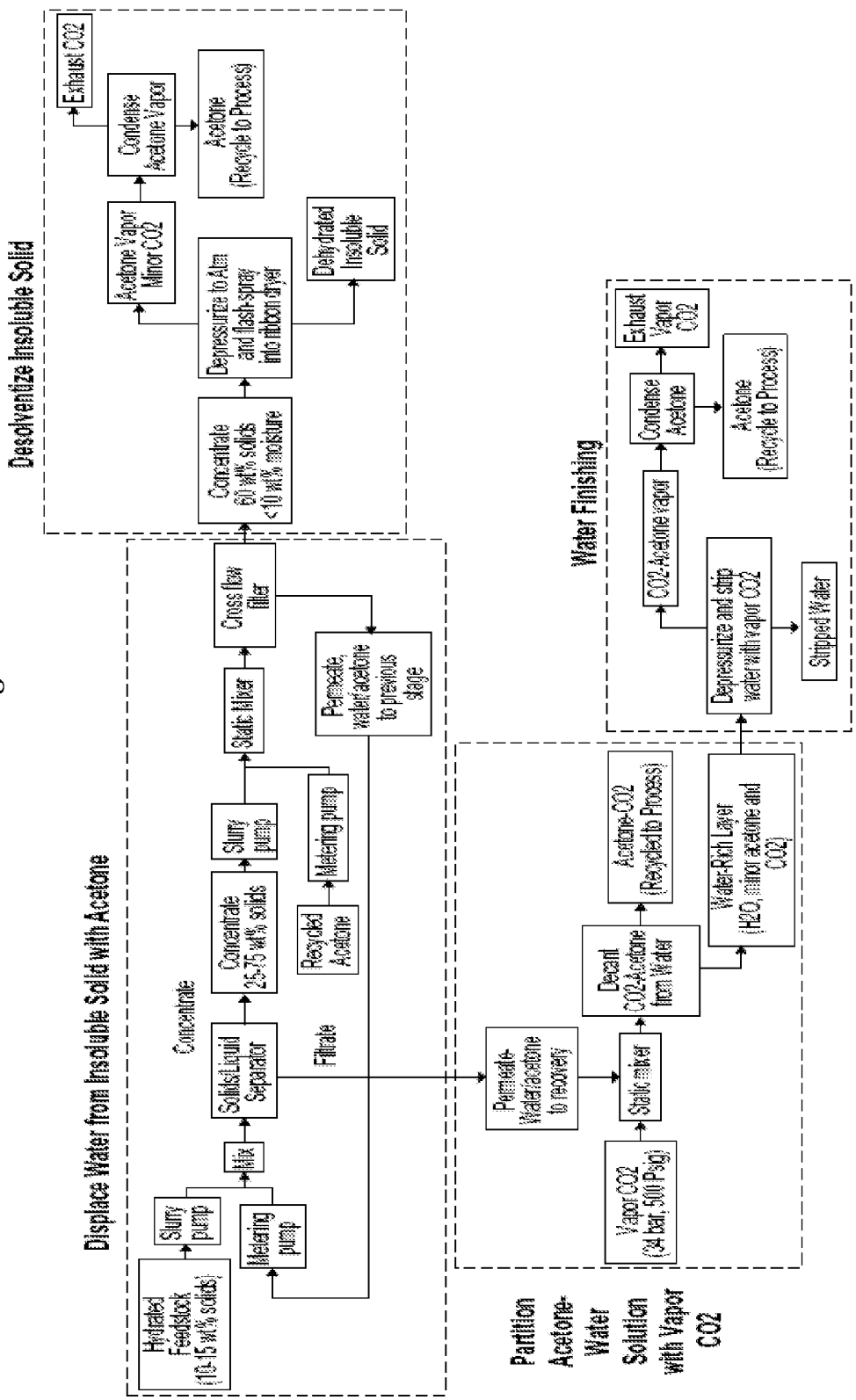
FIG. 2 illustrates exemplary details for the four major process operations with one particular implementation. In this exemplification, the displacement of water is accomplished in two stages. However, one or more stages could be performed. The desolventizing step uses an exemplary flash spray into a ribbon dryer. This is a thermal method to achieve phase conversion. The desolventizing step could be performed, e.g., thermally or via carbon dioxide extraction. The water finishing uses $CO_2$ vapor to strip the residual acetone from the water. This vapor stream is condensed to recover pure acetone to be recycled. The stripped water could be reused or is safe for disposal.
Figure 3:
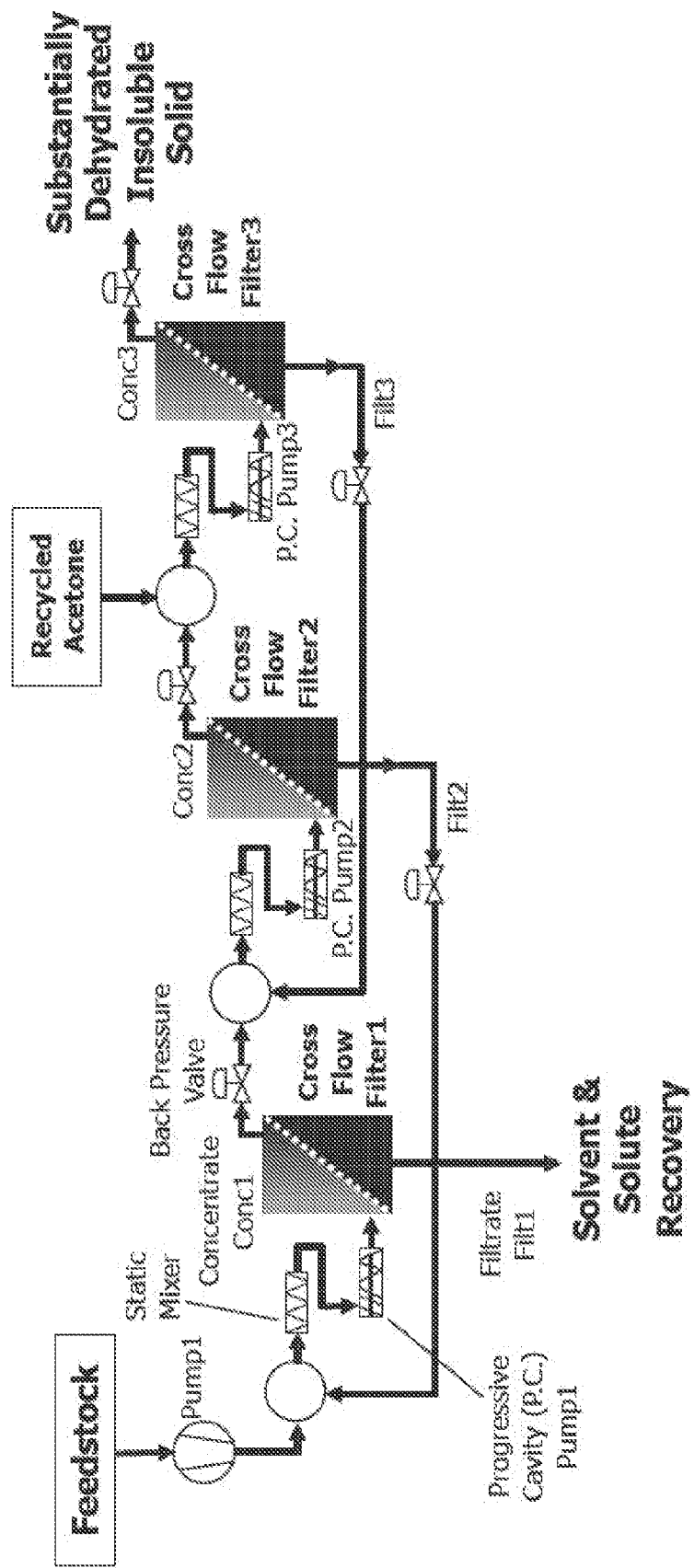
FIG. 3 illustrates an exemplary implementation for displacing water from insoluble solid. In this case, recycled acetone is used in a three stage system of cross-flow filters. The resultant concentrate (Conc3) is substantially dehydrated insoluble solid. This stream would have liquid (acetone-water solution) holdup on the insoluble solids of between 0.75 to 3.0 times the weight of the liquid-free insoluble solid. The Filtrate (Filt1) would go to Solvent & Solute Recovery, i.e., the Partition and Decant and/or Water Finishing operations.
Figure 4:
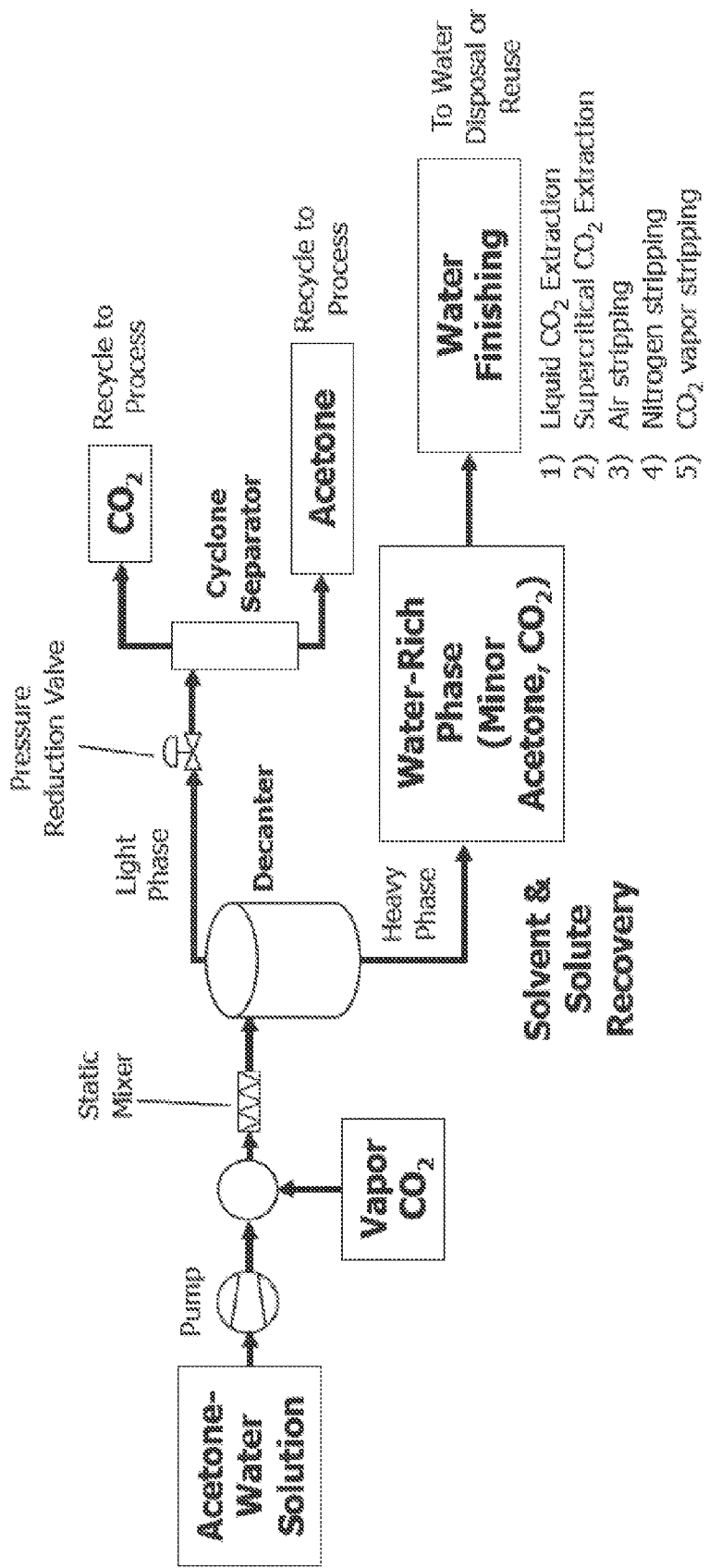
FIG. 4 illustrates an exemplary implementation for acetone recovery. Most of the figure shows the method for implementing the Partition and Decant Operation. The water-rich phase is removed from the Decanter and can go to Water Finishing. Any method known in the art finds use in the Water Finishing step, including without limitation liquid carbon dioxide extraction, supercritical carbon dioxide extraction, air stripping, steam injection, nitrogen stripping, carbon dioxide vapor stripping, etc. This figure depicts the combining of carbon dioxide with acetone-water solution, mixing, and then settling to enable mechanical and, thus, energy efficient separation of the water and acetone.

The present invention is based, in part, on the surprising and unexpected discovery that vapor phase carbon dioxide can be used to split a monophasic, miscible solution of acetone and water into a biphasic solution comprising an upper acetone-dominated or acetone-rich phase and a lower water-dominated or water-rich phase. Surprisingly, the carbon dioxide disrupts the equilibrium between acetone and water. This discovery allows for energy efficient, economically viable and environmentally responsible drying of various feedstocks at a large-scale or commercial scale level. The processes are suitable for processing volumes requiring hundreds, thousands, tens of thousands, even hundreds of thousands of liters. The present acetone drying, dewatering, or dehydrating processes are energy efficient because they can be carried out at ambient temperatures and without performing distillation at any step. The processes can also be performed in a continuous-flow manner. The processes are economically viable because, in comparison to previous acetone drying processes, lower volumes of acetone can be used and a substantial proportion of the acetone can be recovered and re-used with minimal energy input. The processes are environmentally responsible, because less acetone and less energy is used to dry proportionately higher quantities of feedstock, and greater quantities of acetone are efficiently recovered, keeping it out of the environment.

In preferred embodiments, the methods of the invention are performed as a continuous flow process, wherein materials are continuously flowing from one step to the next. The absence of heating of the feedstock combined with recycling and reuse of materials provides energy savings. In some embodiments, both the carbon dioxide and acetone are recycled and reused. Preferably the entire process is performed at ambient temperatures, i.e., without heating or cooling of the feedstock.

The processes are described using acetone as the drying solvent, although the process can also be executed with acetaldehyde. Solvents that find use have a ketone or aldehyde group and miscibility with water. Use of acetone has the advantage of low cost and convenient availability.

2) Drying Hydrated Feedstock with Acetone
  i) General Characteristics of Hydrated Feedstock The input hydrated feedstocks that are dried, dehydrated or dewatered in the present processes generally are composed of a substantial amount of water, for example, at least about 20 wt %, 30 wt %, 40 wt %, 45 wt %, 50 wt %, 55 wt %, 60 wt %, 65 wt %, 70 wt %, 75 wt %, 80 wt %, 85 wt %, 90 wt %, 95 wt % water.

In various embodiments, the hydrated feedstock may also contain oil or lipids.

Prior to contacting with the acetone, the feedstock can be downsized, e.g., chopped, sliced, diced, macerated, ground, shredded, screened, etc. to an average particle diameter of about 500 μm or less, as needed or desired. The particle size may be as small as an average diameter of about 2 μm, and may be in the range of about 25-500 μm. The feedstock particles can be, but need not be, uniform.

In some instances, excess water is removed from the feedstock before contacting with the acetone. This can be done using any method in the art. For example, the feedstock may be subject to mechanical pressing, crossflow filtration, centrifugation, and/or a sieve or screen to drain excess water before contacting with acetone.

The feedstock can be from any of a number of sources, including without limitation, biomaterials, geological materials, hydrocarbon-laden materials, and wastewater streams.

(1) Biological Matter

In some embodiments, the feedstock is biological matter. For example, the biological matter can be without limitation, animal, plant, fungal or bacterial matter, prokaryotic or eukaryotic, edible or non-edible. Biological matter feedstock may contain between about 5-20 wt % solids.

In some embodiments, the biological matter is a mass (e.g., a cake, a paste, a slurry, depending on the amount of water present) a culture of single-celled organisms, e.g., a mass of yeast cells, bacterial cells or algae cells. In some embodiments, the methods find use in the dewatering or dehydrating of harvested algae cells, for example, algae used in the production of biofuels. The algae cells can be cracked or uncracked (i.e., the extracellular membrane is disrupted or breached in cracked algae). In some embodiments, the microalgae are photosynthetic algae. In some embodiments, the microalgae is from a microalgal strain selected from the group consisting of *Dunaliella, Chlorella, Tetraselmis, Botryococcus, Haematococcus, Phaeodactylum, Skeletonema, Chaetoceros, Isochrysis, Selenestrum, Scenedesmus, Nannochloropsis, Nannochloris, Pavlova, Nitzschia, Pleurochrysis, Chlamydomas* or *Synechocystis*. In some embodiments, the microalgae is from a microalgal strain selected from the group consisting of *Selenestrum, Scenedesmus, Nannochloropsis* or *Isochrysis*. In some embodiments, the microalgae is *Nannochloropsis*.

In some embodiments the plant matter is fruit or vegetable matter. For example, the plant matter can be selected from tuber vegetables (e.g., potatoes), root or family Apiaceae vegetables (e.g., carrots, parsnips, turnips, beets, fennel, celery, celeriac, etc), crucifers or brassica or family Brassicaceae vegetables (e.g., broccoli, cauliflower, cabbage, collards, rutabaga, brussels sprouts, radish, etc.), family Liliaceae vegetables (e.g., onions, garlic, leeks, shallots, chives, asparagus), nightshade or family Solanaceae vegetables (e.g., tomatoes, eggplant, capsicum peppers, etc.) and/or family Cucurbitaceae vegetables (e.g., cucumbers, watermelons, melons, squash, marrow, etc.).

In some embodiments, the biological matter is an animal or meat product (e.g., beef, veal, pork, mutton, lamb, poultry, fish, crustaceans, etc.).

(2) Hydrocarbon-Laden Matter

The present processes also find use in decontaminating water and removing hydrocarbons from geological matter. For example, in some embodiments, the feedstock is from a tar sands tailings pond. Such ponds are filled with water contaminated with salts, organic compounds, bitumen, alkanes, and asphaltenes. In this case, the acetone could be used to extract the organic compounds, bitumen, alkanes, and asphaltenes from the water, and carbon dioxide can be used to separate the acetone from the water. Distillation may be required to separate the acetone from the extracted organic compounds, bitumen, alkanes, and asphaltenes.

(3) Geologic Matter

The present processes also find use in decontaminating water and removing hydrocarbons from geological matter. For example, in some embodiments, the feedstock is from mining slurry, including gravel or gypsum. Such mining slurries with water may be contaminated with salts, organic compounds and heavy metals. In this case, the acetone could be used to extract the organic compounds from the water, and carbon dioxide can be used to separate the acetone from the water.

(4) Wastewater Streams

The present processes also find use in decontaminating water from natural gas well fracturing operations. Such natural gas wells are filled with water contaminated with organic compounds and inorganic salts. In this case, the acetone could be used to extract the organic compounds from the water, and carbon dioxide can be used to separate the acetone from the water. Distillation may be required to separate the acetone from the extracted organic compounds.

3) Contacting Feedstock with Acetone

The feedstock is contacted with the acetone under conditions sufficient to extract the water from the feedstock, i.e., for the acetone to replace the water in the feedstock.

Usually, about equal parts by weight acetone and feedstock are mixed together. In some embodiments, smaller quantities of acetone can be added. The acetone and water form a miscible solution containing at least about 30 wt % acetone, for example at least about 35 wt %, 40 wt %, 45 wt % or 50 wt %. At most, sufficient acetone can be added to dilute the water in the feedstock by about 10-fold. Usually, much smaller volumes of acetone are needed, for example, diluting the water in the feedstock by about 5-fold, 4-fold, 3-fold, 2-fold or 1-fold. Efficiency of the process can be improved by performing one or more dilution and separation iterations or stages, wherein acetone is added to the feedstock, and then the feedstock is separated from the excess acetone. This allows for significant reduction in the overall amount of acetone needed for dewatering or dehydrating.

The acetone and hydrated feedstock can be mixed or agitated sufficient to form a miscible acetone-water solution using any method known in the art. In some embodiments, the mixing of the acetone and feedstock is accomplished using a batch mixing tank, an in-line mixer, or a static mixer. Input streams would be the feedstock and new acetone and/or recovered and reused acetone. Output streams would be an aqueous solution of acetone and water and a slurry of insoluble solid saturated with the acetone-water solution. In some embodiments, the mixing of the acetone and feedstock is accomplished using an in-line mixer. Mixing can be accomplished using mechanical means, for example, paddles and a motor. Mixing can also be accomplished using static mixers. Static mixers, or motionless mixers, are fins, obstructions, or channels mounted in pipes, designed to promote mixing as fluid flows through the mixer. Most static mixers use some method of first dividing the flow, then rotating, channeling, or diverting the flow, before recombining it. Other static mixers create additional turbulence to enhance mixing. Mixing can also be accomplished by shaking, spinning or rocking Mixing can be performed in a vessel, e.g., for batch processing, or in a pipe, e.g., for continuous flow processing.

The mixing is typically carried out at ambient temperature, for example in the range of about 20-35° C., for example, about 25-30° C. As desired or needed, mixing can be performed at temperature below ambient in range of 0 to 20° C. As desired or needed, mixing may also be performed at temperature above ambient, for example from 30 to 60° C. The maximum temperature is preferably below the degradation temperature of either the acetone or water soluble constituents or the insoluble solid constituents in the hydrated feedstock. The mixing can be performed at ambient pressure, or under pressurized conditions, as needed or desired. Mixing is performed for an amount of time sufficient to mix the acetone and hydrated feedstock into a uniform or homogenous slurry comprising an acetone-water aqueous solution.

The acetone may also extract other acetone-soluble chemical constituents in addition to water. For example, carotenoids, flavonoids, organic compounds, alkanes and/or hydrocarbons may also be extracted by the acetone.

4) Concentrating the Acetone-Saturated Insoluble Solids in the Acetone-Water Aqueous Solution In some embodiments, the insoluble solids of the feedstock is subjected to acetone extraction is concentrated, and optionally, separated from the superfluous acetone-water aqueous solution (e.g., the filtrate). The liquid separated from the concentrated insoluble solids is referred to as "filtrate." The filtrate is a solution of acetone, acetone-soluble components and water. After filtration, the remaining insoluble solids will be filled with the acetone-water solution in the interstitial spaces around the solid, and the acetone-water solution may be absorbed by the solid. This liquid remaining in and around the insoluble solids after the removal of the filtrate is referred to as "hold up."

The steps of extraction of the feedstock with acetone, concentration of the insoluble solid, and separation of the concentrated insoluble solid from the acetone-water aqueous solution can be performed one or more times, for example, 1, 2, 3, 4, 5 or more extraction and separation iterations, as needed or desired. After concentration, insoluble solids content in the slurry can be increased to at least about 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, and higher, depending on the starting concentration of insoluble solids in the slurry exposed to the acetone and/or the number of iterations of acetone extraction and separation that have been performed. Generally, the higher the starting concentration of insoluble solids, or the greater the number of extraction and concentration iterations, the higher the concentration of insoluble solids in the slurry. The insoluble solids may be concentrated as much as 25%, 50%, 1-fold, 2-fold, 3-fold, 4-fold, 5-fold, 6-fold, 7-fold, 8-fold, 9-fold, 10-fold, or more, e.g., in comparison to the hydrated feedstock or insoluble solids input before performing the one or more iterations of the concentration step.

The concentration of the acetone-saturated insoluble solid from the acetone-water aqueous solution can be accomplished by any method known in the art. For example, the solid can be mechanically concentrated and separated from the superfluous acetone-water aqueous solution using settling and decantation, filter press, belt press, crossflow filtration, screens, sieves, centrifugation or any other mechanical filtration technique. In some embodiments, the insoluble solids are concentrated and separated from the superfluous acetone-water aqueous solution using crossflow or tangential flow filtration. Crossflow filters are known in the art, and are commercially available, e.g. from Graver Technologies, Glasgow, Del. The filter should have a pore size large enough to minimize clogging and small enough to retain the insoluble solids. In some embodiments, the filter has a pore size of about 0.02 µm, 0.05 µm, 0.1 µm, 0.5 µm, 1.0 µm, 5.0 µm, 10.0 µm, 50 µm, or 100 µm, as appropriate for the feedstock or insoluble solids.

The concentration and separation of the acetone-saturated insoluble solids from the superfluous acetone-water aqueous solution is typically carried out at ambient temperature, for example in the range of about 20-35° C., for example, about 25-30° C. The concentration and separation of the acetone-saturated insoluble solids from the superfluous acetone-water aqueous solution can also be performed at ambient pressure. The step of concentrating of the acetone-saturated insoluble solids from the superfluous acetone-water aqueous solution is performed for an amount of time and/or for a number of iterations sufficient to concentrate the insoluble solids to a desired concentration level of solids. The excess acetone-water aqueous solution can then be separated from the concentrated solids.

The steps of concentration and separation of the acetone-saturated insoluble solids from the acetone-water aqueous solution can be performed in a batch process or continuous flow manner.

5) Removal of Acetone from the Insoluble Solid

The acetone saturating the insoluble solids (i.e., the hold up) can be removed from the insoluble solids using any method in the art. In some embodiments, the acetone and residual water (i.e., the hold up) is removed or displaced from the acetone-saturated insoluble solid with liquid-phase or low supercritical phase carbon dioxide. Typically, the acetone-saturated insoluble solid will contain at least about 30 wt % acetone, for example, at least about 35 wt %, 40 wt %, 45 wt %, 50 wt % acetone.

The acetone-saturated insoluble solid is loaded into a chamber that is pressurized to a pressure sufficient for liquid-phase carbon dioxide at the working temperature. Extraction of acetone with liquid-phase can be carried out at ambient temperature, for example in the range of about 20-35° C. or about 25-30° C. In various embodiments, the working temperature is in the range of about 20-55° C., for example, about 20° C., 21° C., 22° C., 23° C., 24° C., 25° C., 26° C., 27° C., 28° C., 29° C., 30° C., 31° C., 32° C., 33° C., 34° C., 35° C., 40° C., 42° C., 45° C., 48° C., 50° C., 52° C. or 55° C. The pressure in the chamber will generally be in the range of about 500 to about 3000 psi (about 34.5 to about 207 bar), for example, about 500 psi, 600 psi, 700 psi, 800 psi, 1000 psi, 1500 psi, 2000 psi, 2500 psi or 3000 psi. In some embodiments, the chamber is pressurized to at least about 850 psi (at least about 60 bar). In some embodiments, the temperature and pressure in the pressurized chamber are sufficient to maintain carbon dioxide in its supercritical phase. In one embodiment, the pressure and temperature are maintained at about 1500 psi (100 bar) and 55° C., respectively.

Certain biological substrates adsorb acetone into the biomass. Examples are plant biomass (e.g., spinach, kale, onions, red pepper, etc.), and animal biomass (e.g., mussels). Residual acetone can be removed from biomass that adsorbs acetone by contacting the acetone-saturated biomass with carbon dioxide at slightly above the critical point (i.e., about 100 bar pressure and approximately 50-60° C.). Without being bound to theory, the adsorption of acetone into biomass may be related to collapsing pores in the solid biomass under supercritical pressures, thereby decreasing the effective porosity of the biomass and inhibiting the infusion and desorption of acetone from the biomass. When the pressure is decreased from supercritical levels to critical levels in the temperature range of about 50-60° C., the carbon dioxide goes from the supercritical phase ($SCCO_2$) to the vapor phase, avoiding the liquid $CO_2$ phase and the associated surface tension. By definition, the surface tension of the $SCCO_2$ and vapor $CO_2$ is zero. This avoids collapse of the pore structure and enables the acetone to be better extracted from the porous biomass.

Liquid-phase or supercritical phase carbon dioxide is then added to the pressurized chamber. The liquid-phase or supercritical phase carbon dioxide extracts or "strips" the acetone from the water in the acetone-water solution and from the interstitial space in the acetone-saturated insoluble solid. The carbon dioxide is added at a solvent to insoluble solids ratio, i.e., solvent-to-feed ratio, in the range of about 0.8 to about 10, for example, a solvent-to-feed ratio of about 0.8, 1.0, 2.0, 3.0, 4.0, 5.0, 6.0, 7.0, 8.0, 9.0 or 10.0.

Extraction of acetone from the acetone-saturated insoluble solid with carbon dioxide is performed under conditions sufficient to extract a majority of or substantially all of the acetone from the insoluble solid. Extraction of acetone from the acetone-saturated insoluble solid or the hold up with carbon dioxide can be carried out in batches or as part of a continuous flow process. One or more iterative extractions of the acetone with liquid-phase carbon dioxide may be performed. In some embodiments, 1, 2, 3, 4, 5 or more iterative liquid-phase carbon dioxide extractions of acetone from the hold up and/or the aqueous solution separated from the hold up (comprising acetone, water and carbon dioxide) are performed, as need or desired.

In one embodiment, the acetone is extracted from the acetone-saturated insoluble solid using a pressurized chamber containing an inclined auger. This has been described, e.g., in U.S. Patent Publication No. 2008/0251454. Briefly, the insoluble solid would be exposed to liquid-phase or biphasic dense phase carbon dioxide in a pressurized tubular chamber comprising the inclined auger. The liquid-phase carbon dioxide extracts insoluble solids in the bottom half of the chamber. As the auger turns, the insoluble solids are conveyed to the top of the chamber, above and away from the liquid phase carbon dioxide, and expelled from the top end of the tubular chamber, thereby extracting the acetone from the insoluble solids and separating the insoluble solids from the aqueous solution comprising acetone, water and carbon dioxide.

In one embodiment, the acetone is extracted from the acetone-saturated insoluble solids using a suitable filtration system. Use of a filtration system may be more appropriate when the insoluble solids are particularly small (e.g., about 100 μm or smaller) and/or have a low Stokes settling velocity relative to the volumetric flow of the carbon dioxide (e.g., a settling velocity of less than about 10 cm/min). Suitable filtration systems are known in the art, e.g., crossflow filters, bag filters, cartridge filters, and can be used to trap insoluble solid particulates entrained in the carbon dioxide. In some embodiments, the acetone-saturated insoluble solids are extracted with liquid phase carbon dioxide via a crossflow filtration system.

In some embodiments, extractions of acetone-saturated insoluble solids with carbon dioxide combine the use of the inclined mechanical auger and a filtration system. For example, the acetone in the acetone-saturated insoluble solids could first be extracted with liquid-phase or biphasic dense phase carbon dioxide using the inclined mechanical auger. Insoluble solid particulate that was not separated from the remaining aqueous solution by the inclined auger could be further extracted with liquid phase carbon using a suitable filtration system, e.g., by crossflow filtration.

On treatment of the insoluble solids with carbon dioxide, the acetone content in the insoluble solids can be reduced to about 5 ppm or less, for example, about 4 ppm, 3 ppm, 2 ppm, 1 ppm, or less.

In some embodiments, the acetone in the aqueous solution comprising acetone, water and carbon dioxide (i.e., the filtrate) is further "stripped" or removed from the water with one or more additional extractions with carbon dioxide. The distribution coefficient of the acetone for the liquid-phase carbon dioxide in the carbon dioxide/acetone/water solution is between about 3.5-5.0, favoring the transfer of the acetone from the water to the carbon dioxide. Further extractions of the aqueous solution separated from the insoluble solids can be performed using any method known in the art. In one embodiment, the aqueous solution comprising acetone, water and carbon dioxide is further extracted with liquid-phase carbon dioxide in a countercurrent column system.

In another embodiment, the acetone or acetone/water holdup in the insoluble solid can be removed thermally. There would still be an energy advantage over traditional spray or drum drying methods because the heat of vaporization of acetone (534 kJ/kg at 25° C. is much less than water (2547 kJ/kg at 25° C.).

6) Recovery of Carbon Dioxide from Aqueous Solution and Insoluble Solids

In some embodiments, the carbon dioxide used to extract the acetone from the acetone-saturated insoluble solids and to strip the acetone from the water in the aqueous solution of the filtrate is recovered. The carbon dioxide can be recovered using any method known in the art. Preferably, the carbon dioxide is recovered at ambient temperature, i.e., without any input of heat energy.

For example, the aqueous solution comprising acetone/water/carbon dioxide and/or the carbon dioxide-saturated insoluble solids can be depressurized, so that the carbon dioxide is converted to the vapor phase and released, leaving an aqueous solution of acetone (with acetone-soluble extractants) and water. For example, at ambient temperature, the aqueous solution and/or insoluble solids can be subject to a pressure of less than about 35 bar, less than about 30, 25, 20, 15, 10, 5 bar, or the pressure returned to ambient pressure, thereby vaporizing and releasing the carbon dioxide from the solution and/or the solids.

The release of the carbon dioxide from the insoluble solids yields insoluble solids that are dehydrated or dewatered, with water and acetone effectively removed.

Carbon dioxide that has been vaporized can be collected, condensed back to the appropriate phase by appropriately changing the temperature and/or pressure, and recycled. The recycled carbon dioxide can be reused for the extraction of acetone from acetone-saturated insoluble solids. The energy efficiency of the vaporization-condensation cycle of the recycled carbon dioxide can be increased by the concurrent use of a heat pump. See, e.g., U.S. Patent Publication No. 2009/0166175 and PCT Application No. PCT/US2008/087649, published as WO 2009/086082.

In an alternative embodiment, the acetone/water/carbon dioxide aqueous solution and/or the insoluble solids are flashed to recover the acetone and recycle the carbon dioxide. This embodiment is less preferred because it is less energy efficient and may subject the insoluble solids to unacceptably high temperatures.

Prior to release of the carbon dioxide from the aqueous solution, the filtrates from the one or more extractions of the acetone-saturated insoluble can be combined.

7) Recovery of Acetone from Aqueous Solution

The invention avoids the use of energy inefficient distillation for the recovery of acetone and leverages the unique phase behavior of acetone, water, and carbon dioxide. It has been surprisingly discovered that vapor phase carbon dioxide disrupts the equilibrium between acetone and water in an aqueous solution. When the ternary system of acetone/water/carbon dioxide is created, the system splits into two liquid phases. The higher density phase is water-dominated (water-rich). The lower density phase is acetone-dominated (acetone-rich). By leveraging this equilibrium behavior, the acetone-rich layer can be readily physically separated from the water-rich layer. The water is physically separated rather than acetone being extracted from the water by the carbon dioxide. Using the present methods, the acetone used to dehydrate the feedstock is recovered without distillation and preferably at ambient temperatures. The recovered acetone can be recycled and reused for extracting further feedstock.

An acetone-water aqueous solution comprising at least about 30 wt %, 35 wt %, 40 wt %, 45 wt %, 50 wt % acetone and at least about 40 wt %, 45 wt %, 50 wt % water is pumped into a chamber that is pressurized to a pressure sufficient for vapor phase, liquid-phase or supercritical phase carbon dioxide at the working temperature. The recovery of the acetone can be carried out in batch processing or as part of a continuous flow process. In some embodiments, the chamber is a vessel or a batch tank. In some embodiments, the chamber is a countercurrent column.

Recovery of the acetone from the aqueous solution is preferably carried out at ambient temperature, for example in the range of about 20-35° C., for example, about 25-30° C., which is below the critical temperature of carbon dioxide. In some embodiments, the ambient temperature is about 20° C., 21° C., 22° C., 23° C., 24° C., 25° C., 26° C., 27° C., 28° C., 29° C., 30° C., 31° C., 32° C., 33° C., 34° C. or 35° C. At ambient temperatures, the pressure in the chamber will generally be in the range of about 0.2 times to about 10 times the vapor pressure (e.g., about 13 to about 650 bar), for example, about 0.3 to about 5 times (e.g., about 20 to about 325 bar), about 0.5 to about 2 times (e.g., about 32 to about 130 bar), or about 0.75 to about 1.25 times (e.g., about 48 to about 82 bar), the vapor pressure of the carbon dioxide. In some embodiments, the step of acetone recovery is performed at a pressure that is below the vapor pressure of carbon dioxide. In some embodiments, the step of acetone recovery is performed at a pressure that is about 0.5 to about 0.95 the vapor pressure of carbon dioxide (e.g., about 30 to about 60 bar), for example, about 0.75 to about 0.95 the vapor pressure of carbon dioxide (e.g., about 48 to about 60 bar). In some embodiments, the step of acetone recovery is performed at a pressure that is about 10 to about 69 bar, for example, from about 34 to about 69 bar, for example, from about 10 to 30 bar. In some embodiments, the step of acetone recovery is performed at a pressure that is about 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 bar.

In some embodiments, recovery of the acetone from the aqueous solution is performed at a temperature above the critical temperature of carbon dioxide, i.e., above 31.1° C. Above the critical temperature for carbon dioxide, the pressure in the chamber will generally be in the range of about 0.2 times to about 10 times the critical pressure (e.g., about 15 to about 730 bar), for example, about 0.2 to about 5 times (e.g., about 15 to about 365 bar), about 0.5 to about 2 times (e.g., about 36 to about 146 bar), about 0.75 to about 1.25 times (e.g., about 55 to about 92 bar), or about 0.75 to about 0.95 (e.g., about 55 to about 70 bar) the critical pressure of the carbon dioxide.

The carbon dioxide is introduced into the chamber in an amount in the range of about 10 wt % to about 50 wt % of the mass of the acetone-water aqueous solution, for example, about 10 wt %, 15 wt %, 20 wt %, 25 wt %, 30 wt %, 35 wt %, 40 wt %, 45 wt %, 50 wt %. In some embodiments, the composition of the ternary composition comprising acetone/$H_2O$/$CO_2$ is in the range of about 25 wt %/50 wt %/25 wt % to about 35 wt %/15 wt %/50 wt % (i.e., about 25-35 wt % acetone, about 15-50 wt % water and about 25-50 wt % carbon dioxide). The carbon dioxide disrupts the equilibrium between the acetone and water in the acetone-water solution and shifts the phase behavior of the acetone-water mixture. With the creation of the ternary system (water, acetone, carbon dioxide), the carbon dioxide causes the previously miscible water and acetone to form an acetone-rich solution (acetone and minor components of carbon dioxide and water) and a water-rich solution (water and minor components of carbon dioxide and acetone). In some embodiments, the acetone-rich phase can contain less than about 2 wt % $H_2O$. In some embodiments, the water-rich phase can contain less than about 5 wt % acetone, for example, less than about 4%, 3%, 2%, 1%, acetone.

In some embodiments, the phase split can be achieved at temperature below the critical temperature and above the vapor pressure (i.e., using liquid-phase $CO_2$). In some embodiments, the phase split can be achieved at a temperature in excess of the critical temperature and critical pressure (i.e., the peak of the vapor pressure curve or supercritical phase $CO_2$).

The separation of acetone-water mixtures with carbon dioxide contrasts with separating ethanol-water mixtures with carbon dioxide. In the case of ethanol-water separation, the addition of liquid or supercritical carbon dioxide does achieve a phase split. However, substantial ethanol remains in the water-rich phase. Also, ethanol-water separation using carbon dioxide requires a higher $CO_2$ to feed (EtOH/$H_2O$) ratio to substantially deplete the concentration of ethanol in water-rich phase.

The acetone rich phase can be conveniently separated from the water rich phase using any method known in the art. Physical separation techniques of use for phase separation are known in the art and include without limitation decantation, membrane filtration, cyclonic separation, and centrifuging.

Once separated, the acetone-rich phase can be reused for further dehydrating extractions of water from fresh feedstock input. Because acetone-soluble components may have been co-extracted with the acetone (e.g., carotenoids, flavonoids, organic compounds, hydrocarbons, etc.), in some embodiments it may be desirable to further extract these acetone-soluble components from the separated acetone-rich phase. This can be accomplished using any method known in the art. For example, the acetone-rich phase can be distilled or further extracted with liquid-phase carbon dioxide, e.g., in a countercurrent column.

In some embodiments, the water-rich phase can be treated, at atmospheric pressure, with air, nitrogen, carbon dioxide, or other gas sparging techniques to remove residual acetone that remains in the water-rich phase after physical separation. The water-rich phase may contain between 1 wt % and 10 wt % residual acetone. Any method known in the art finds use in the water finishing step, which removes residual acetone. Illustrative finishing techniques include without limitation liquid carbon dioxide extraction, supercritical carbon dioxide extraction, air stripping, steam stripping, nitrogen stripping, carbon dioxide vapor stripping, etc.

Figure 12:
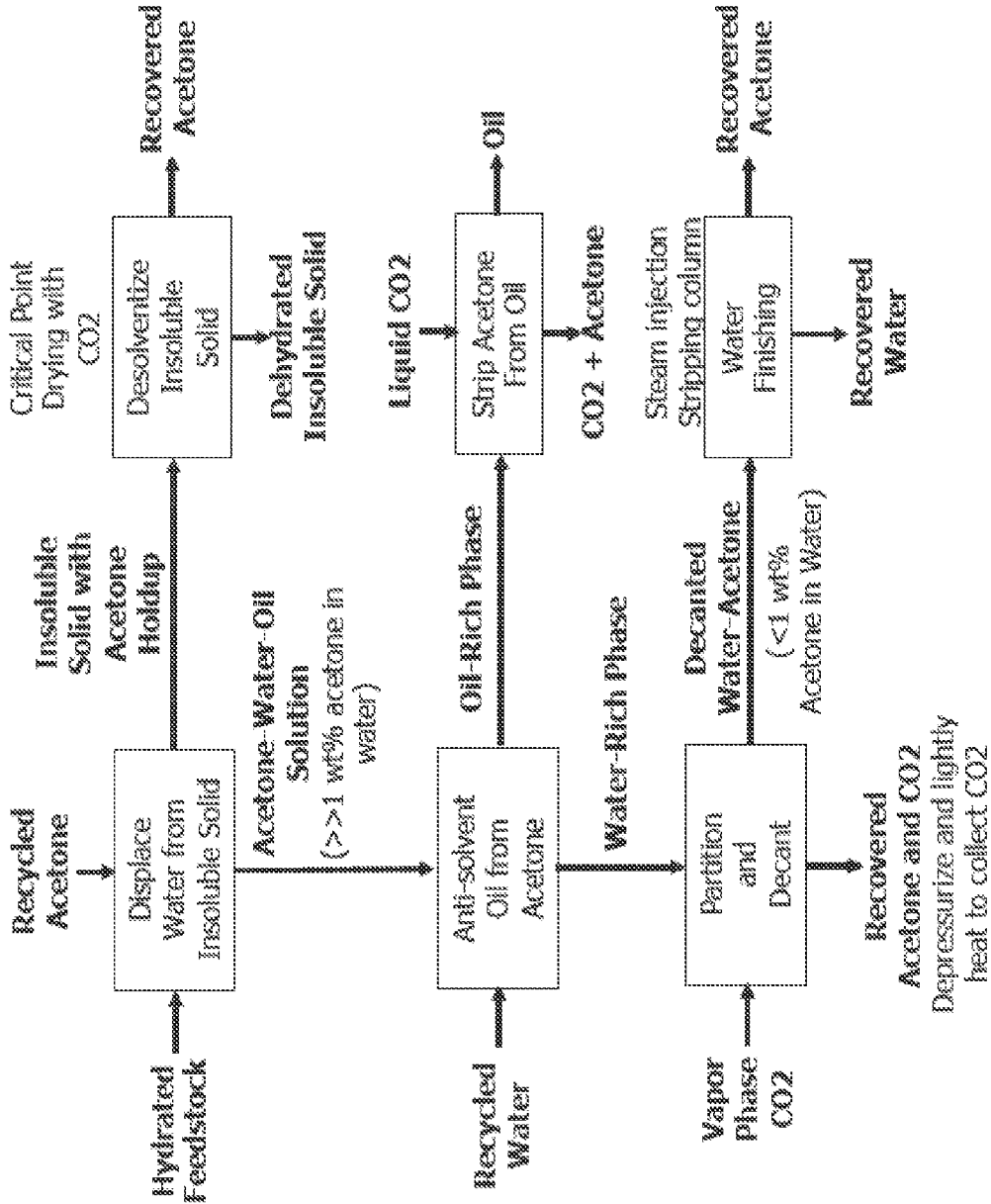
FIG. 12 illustrates the four additional process operations of the present drying process for removing of oil that may be present in the hydrated feedstock.

In embodiments where the hydrated feedstock comprises oil, the oil in the acetone-water-oil mixture can first be removed by contacting the mixture with additional water to form a biphasic solution comprised of an oil-rich phase comprising acetone and oil, and a water-rich phase comprising water and acetone. The oil rich phase is contacted with liquid-phase carbon dioxide to strip the acetone from the oil. The water-rich phase is contacted with vapor phase carbon dioxide, as described herein. An illustrative flow diagram of this process is depicted in FIG. 12.

EXAMPLES

The following examples are offered to illustrate, but not to limit the claimed invention.

Example 1

Exemplary Apparatus and Drying of *Nannochloropsis*

Figure 5:
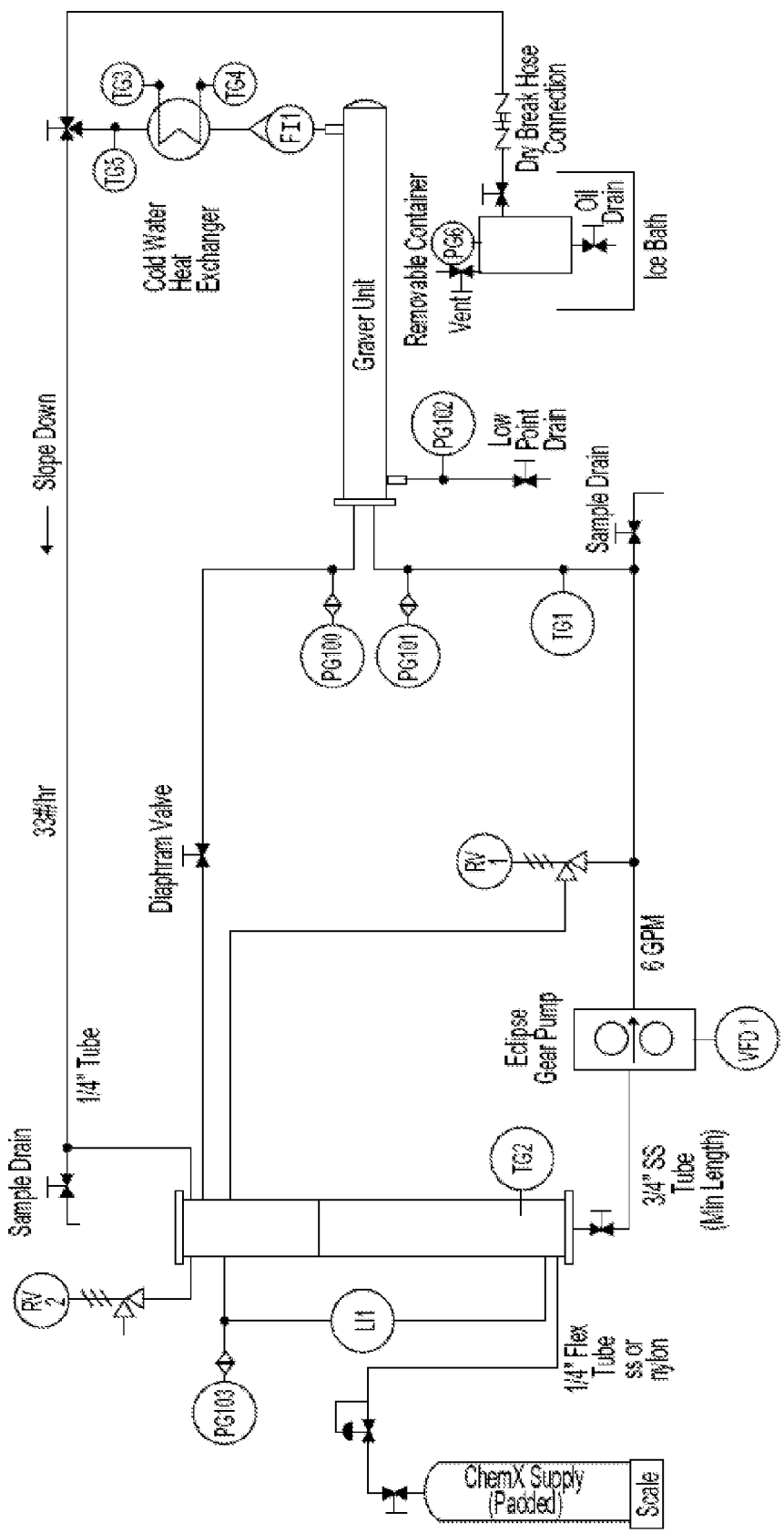
FIG. 5 depicts an exemplary crossflow extraction system for use in the present methods.

An exemplary apparatus to achieve contact between hydrated feedstock and acetone was created. This apparatus uses Graver Technologies Scepter® microfiltration filter with a 0.1 micron nominal pore size. The system is shown in FIG. 5. The system configuration includes a Specter microfiltration membrane, a 6 gal/min (22.8 L/min) Eclipse gear pump by the Pulsafeeder division of IDEX Corporation, a holdup tank with capacity for 3 gallons (11.4 L) of process fluid. The Scepter filter had a 0.0967 $m^2$ (0.75 $ft^2$) filter area. The system enables permeate to be introduced back into the concentrate. The feature allows the degradation of filter flux rate to be evaluated as a function of operating time.

A 4 kg charge of *Nannochloropsis* algae with a solid concentration of 14 wt % and a water content of 96 wt % was processed for drying. The experiment was run with multiple stages, where a stage represents the introduction of acetone, the removal of permeate sample(s), and the collection of a concentrate sample. The experiment was run in a crosscurrent manner. This implies that fresh acetone was used in each stage. The first acetone addition was 4 kg for a solvent to feed ratio (SF) of 1.0. Subsequent additions were of the order 1.7 kg each. A total of 8 stages were run.

Figure 6:
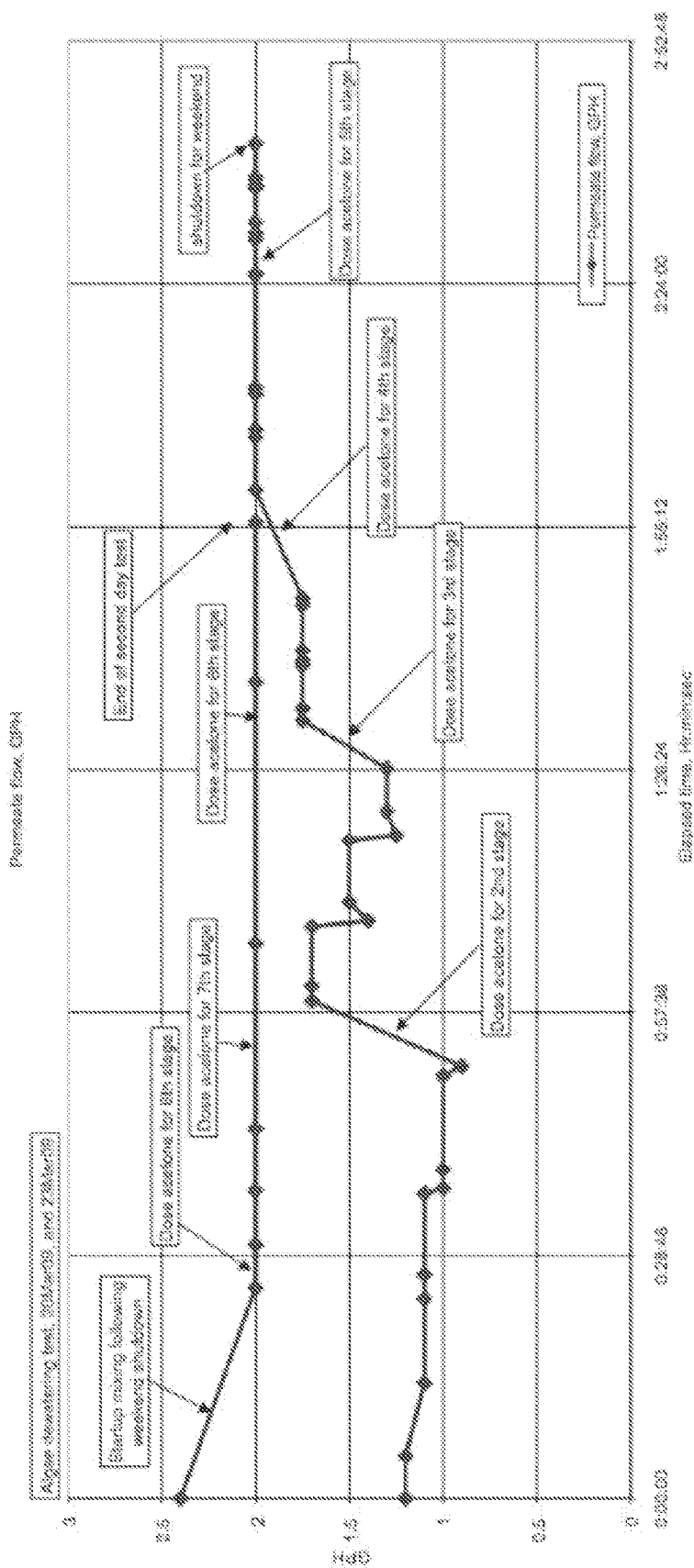
FIG. 6 illustrates an exemplary permeate flow diagram, demonstrating the efficiency of the present drying methods.

Results:

The permeate flow is shown in FIG. 6. During the first stage of extraction, the flow rate was 1 GPH (gallons per hour) or 32 GFD (gallons per square foot per day). This compares with a nominal flow rate of 100 GFD for dewatering of dilute algae (0.1 wt %). The lower flux rate is a function of the increased viscosity due to the higher relative solids content. For the second stage, the flow rate was 1.5 GPH or 48 GFD. For the third state, the flow rate was 1.75 GPH or 56 GFD. For all subsequent stages, the flow rate was 2.0 GPH or 64 GFD. Accounting for the 30% knockdown due to the partially occluded filter, the flux rates would be 46, 69, 80, and 91 GFD for the first, second, third, and all subsequent stages, respectively.

The flux rate increases as a function of time during the test due to the increased dilution by acetone. Acetone lowers the viscosity of the liquid solution, leading to a higher flux rate.

Figure 7:
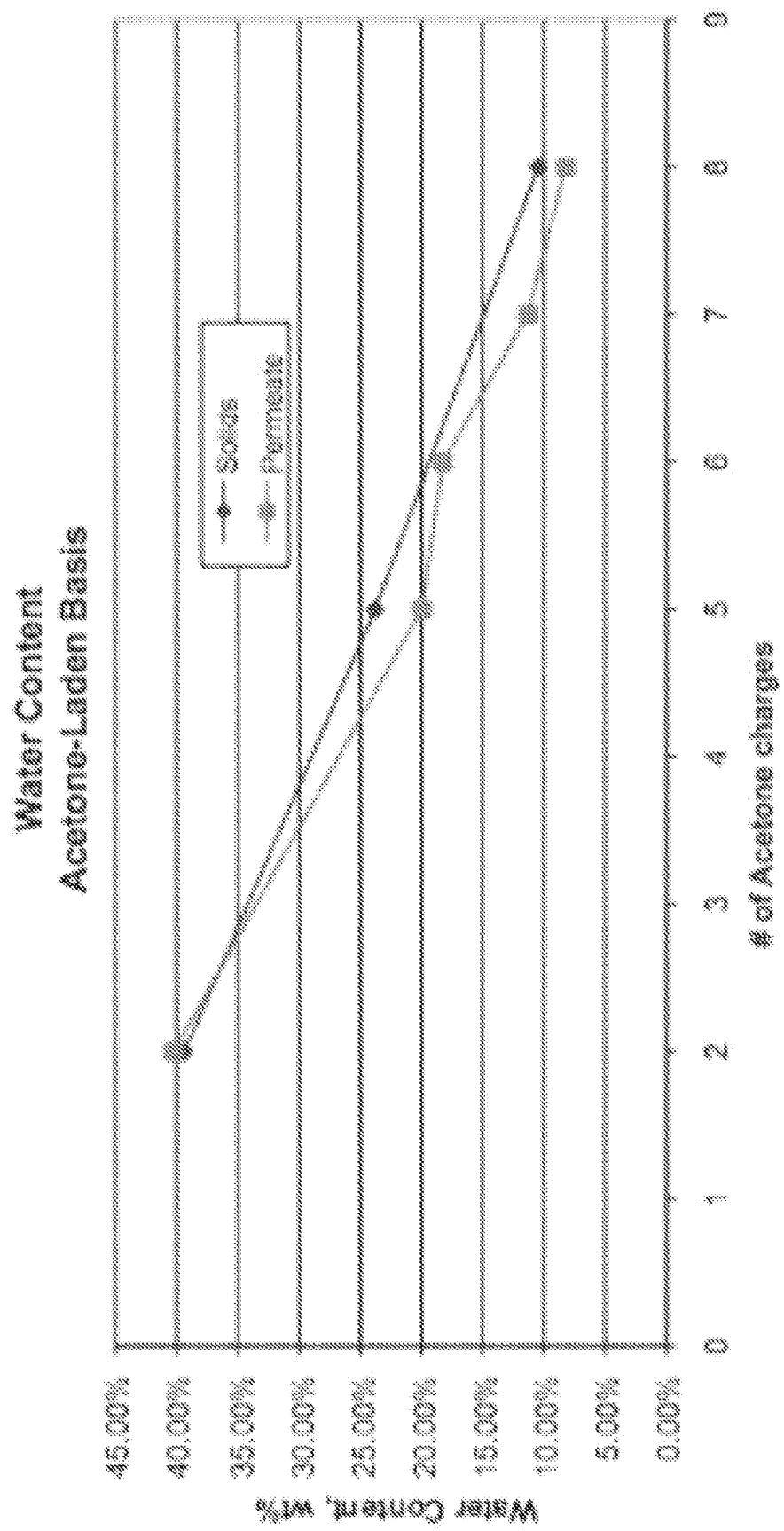
FIG. 7 illustrates water content in solids (concentrate) and permeate samples on an acetone-laden basis after being subject to the present methods.

The water content in the acetone-laden solution for permeate and concentrate is shown in FIG. 7. The water content was determined via Karl Fischer (KF) measurement and was previously shown to have an accuracy of 1%. Each water datum represents the average of five replicates for the permeate and three or four replicates for the solid sample. In the interest of understanding trends, select samples from the crossflow test were tested via KF. Each sample (solids/concentrate and permeate) was tested in the fully acetone-laden state.

Figure 8:
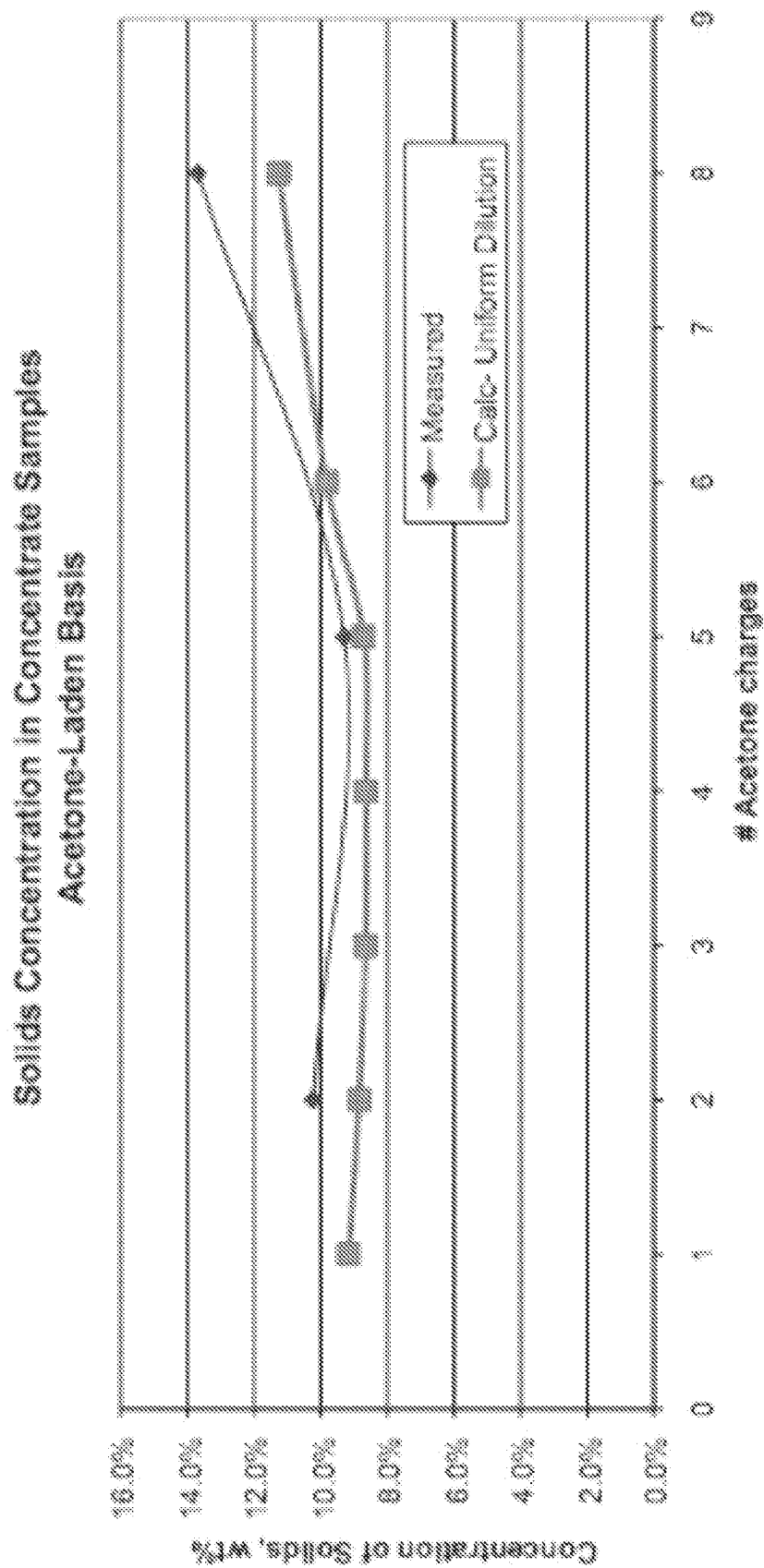
FIG. 8 illustrates water content in concentrate on an acetone-laden basis after being subject to the present methods.

The solids content in the acetone-laden state is shown in FIG. 8. This figure shows the surprising result that the solids concentration, which started at 14 wt % in the algae paste drops to 9 wt % in the first stage and gradually increases through the last stage to approximately 12 wt % in the final stage. The chart shows the solids concentration values that were measured experimentally with loss on dryness (LOD) with a heating temperature of 120° C. At this temperature, both the acetone and water was flashed from the residual solid. The chart shows a calculation of the solids concentration assuming uniform distribution of the water. This ignores the likely difference between extracellular water and intracellular water. It assumes that all the water is uniformly distributed through the system and perfectly mixed (and thus single phase) with the acetone. The experimental data points are in reasonable agreement with the theoretical values.

Figure 9:
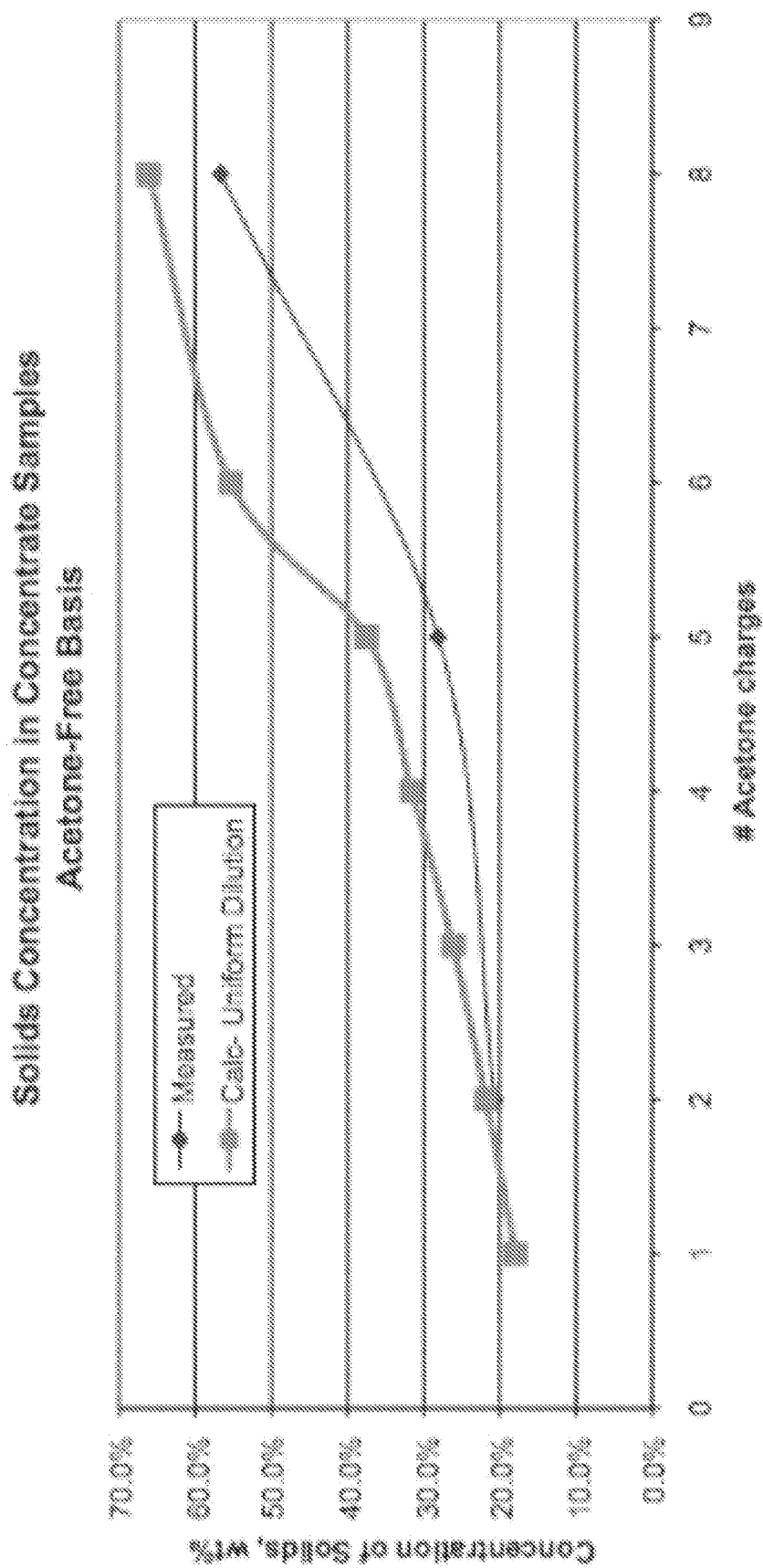
FIG. 9 illustrates water content in concentrate, acetone-free basis after being subject to the present methods.

The solid concentration, on an acetone-free basis, is shown in FIG. 9. This reflects the amount of dried alga solids that would be present if the acetone were removed and the water were left with solid. Again the measured data is in reasonable agreement with the uniform dilution calculation.

The liquid removal in each stage was constrained by the hold up (dead) volume in the system. A minimum quantity of material was required to maintain pump circulation. Thus, the achieved concentrate solids content in each of the stages was lower than the practical maximum. In retrospect, this could have been compensated in the crossflow test by using a larger initial algae charge that would, subsequently, have retained more volume within the system.

Furthermore, subsequent to the final stage, the concentrate was visually examined and thought, because of the low water content and the related high acetone content, to be highly likely to be filterable. Using a Buchner funnel and filter paper, a portion of the eighth stage concentrate was filtered. Half of the mass of the solution was immediately and rapidly drained through the filter paper. This filtration increased the concentration of the fluid to 23 wt % solids (acetone-laden basis) and 72 wt % solids (acetone-free basis).

In addition, the acetone was flashed from the concentrate (at room temperature conditions), making a dried solid material. This material was tested via KF and found to be 9 wt % moisture, an essentially fully dried sample.

The liquid permeate from the test was collected, loaded in a chamber capable of 100 bar (1450 psi) pressure and filled with $CO_2$. At a pressure of 50 bar, the water rich layer separated from the acetone-rich layer. The water-rich layer was drained via a bottom valve in the chamber. This water layer was subjected to air stripping by bubbling compressed air through the water to remove residual acetone present. After air-stripping, the balance of the water was essentially acetone free. The remaining solution in the chamber was acetone, carbon dioxide, and chlorophyll. The carbon dioxide was vented. The remaining acetone was available to be recycled.

Example 2

Drying Carrot Pomace 89.52 g of carrot pomace with a starting moisture content of 88.7 wt % were treated with four stages of acetone drying. In each stage, the feed (carrot pomace and liquid holdup) was combined with water-free acetone. At each stage of the solvent to feed ratio (S/F Ratio) was computed by the mass of carrot slurry feed divided by the mass of acetone. After mixing well, the slurry of pomace and acetone was squeezed through a 1 micron filter to collect filtrate (the liquid fraction) and concentrate (fraction with residual solids). The filtrate was a mixture of water, acetone, and carotenoids. The concentrate was acetone-insoluble solids (such as fiber, carbohydrates, and minerals) with liquid holdup. The holdup was a mixture of acetone and water. In the context of all four stages, a total of 225.16 g of acetone were used for a overall S/F (total acetone/carrot pomace) of 2.52.

In each stage, the amount of concentrate's liquid holdup was measured via a loss on dryness scale operating at 120° C. and, hence, a high enough temperature to vaporize the water and acetone without causing degradation of the remaining solids. Filtrate water content was measured via Karl Fischer and are an average of three measurements. The liquid holdup in the solids was assumed to be same composition as the filtrate. Water content in the solids was computed using the measured liquid holdup in the concentrate.

Table 1, below, shows that after four stages, there was much lower water content in the concentrate. By the fourth stage, the water in carrot pomace concentrate was almost completely displaced by the acetone.

TABLE 1

| | | | | | | | Mass | Filtrate | Concentrate | |
| | | | | | | | | Water | Liquid | Water |
| Stage | Comment | Feed (g) | Acetone (g) | S/F Ratio | Concentrate (g) | Filtrate (g) | Balance (%) | Content (wt %) | Holdup (wt %) | Content (wt %) |
|---|---|---|---|---|---|---|---|---|---|---|
| 0 | Start Material | 89.52 | 0.00 | N.A. | 89.52 | 0.00 | 100% | N.A. | 88.7% | 88.70% |
| 1 | 1st Exchange | 89.52 | 89.46 | 1.00 | 69.09 | 101.39 | 95% | 45.34% | 88.8% | 40.26% |
| 2 | 2nd Exchange | 50.80 | 67.11 | 1.32 | 26.20 | 86.51 | 96% | 19.82% | 79.3% | 15.72% |
| 3 | 3rd Exchange | 17.33 | 44.66 | 2.58 | 14.93 | 42.00 | 92% | 6.15% | 76.9% | 4.73% |
| 4 | 4th Exchange | 7.40 | 23.93 | 3.23 | 7.44 | 20.71 | 90% | 1.88% | 79.4% | 1.49% |

The filtrate from the stages was collected (total mass of 250.61 g). This solution was loaded into a chamber that was pressurized to 100 bar (1450 psia). Carbon dioxide from a storage cylinder was transferred into the chamber and bubbled through the solution. At a pressure of 45 bar (653 psia), the solution split into two phases: lighter acetone-rich phase and a heavier water-rich phase. At this temperature condition, the vapor pressure of carbon dioxide was 64.34 bar (933.2 psia). Using drain valves on the chamber, the water-rich phase was decanted from the acetone-rich phase.

The concentrate from stage four was loaded into a different chamber that was pressurized to 100 bar (1450 psia). Liquid $CO_2$ flowed into the bottom of the chamber and liquid $CO_2$, acetone, and water solution flowed from the top of the chamber. A mass of liquid $CO_2$ equal to 10 times the mass of the concentrate charge flowed through the chamber. This amount of liquid $CO_2$ extracted the acetone and displaced the solution. Liquid $CO_2$ remained as the holdup on the pomace solid. The chamber was vented slowly. The resultant carrot residue was comprised of carrot fiber, carbohydrates, and minerals and was essentially bone dry.

Example 3

Figure 10:
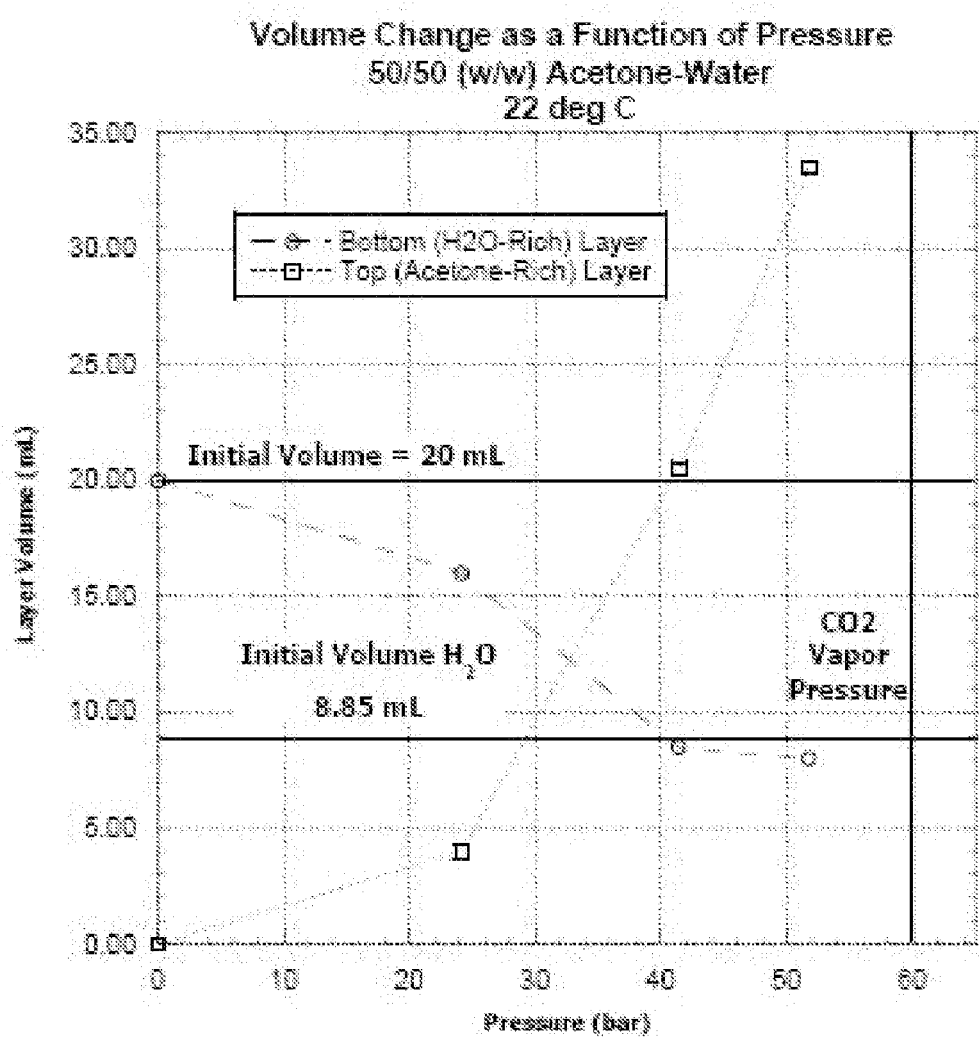
FIG. 10 illustrates that at atmospheric pressure and 22° C., there is only a single phase in an aqueous solution of 50/50 (wt/wt %) acetone/water.

Separation of Acetone and Water in a 50/50 (wt/wt %) Acetone-Water Aqueous Solution A mixture of 50/50 (wt/wt %) acetone-water was created. The density of this solution was measured to be 0.885 kg/L. A 20 mL quantity of this material was charged into a sight glass chamber that enabled introduction of carbon dioxide gas into solution, monitoring of the pressure and temperature within the chamber, decantation of the bottom layer, and direct observation of the solution, number of phases, and the volume of each phase. In the initial 20 mL solution, there was 11.2 mL of acetone and 8.85 mL of water. The temperature in the chamber was maintained at an ambient temperature of 22° C. At this temperature, the vapor pressure of $CO_2$ was 60.031 bar. The graph depicted in FIG. 10 shows that at atmospheric pressure, there was only a single phase. As carbon dioxide was added to the system, raising the system pressure to 25 bar, the solution splits into two phases. At a pressure of approximately 42 bar and well below the vapor pressure of the $CO_2$, the water-rich layer was approximately equal to the original volume of water added to the system. The acetone-rich layer increases in volume in excess of the original volume of acetone due to expansion by carbon dioxide.

The water rich layer was drained from the acetone rich layer. The addition of $CO_2$ below the vapor pressure enables the separation of the water from the acetone.

Example 4

Figure 11:
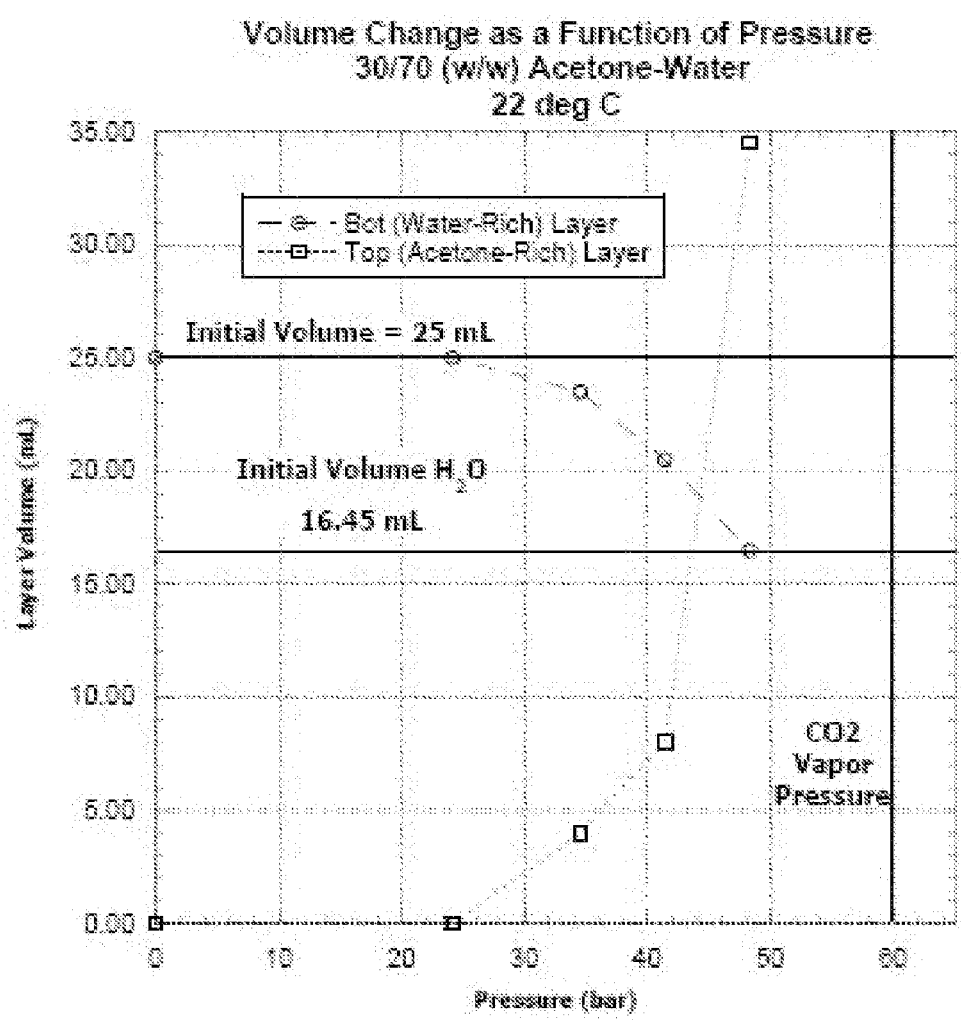
FIG. 11 illustrates that at atmospheric pressure and 22° C., there is only a single phase in an aqueous solution of 30/70 (wt/wt %) acetone/water.

Separation of Acetone and Water in a 30/70 (wt/wt %) Acetone-Water Aqueous Solution A mixture of 30/70 (wt/wt %) acetone-water was created. The density of this solution was measured to be 0.940 kg/L. A 25 mL quantity of this material was charged into the same sight glass chamber as Example #2. In the initial 25 mL solution, there was 8.92 mL of acetone and 16.45 mL of water. The temperature in the chamber was maintained at an ambient temperature of 22° C. At this temperature, the vapor pressure of $CO_2$ was 60.031 bar. The graph depicted in FIG. 11 shows that at atmospheric pressure, there was only a single phase. As carbon dioxide was added to the system, raising the system pressure to 35 bar, the solution splits into two phases. At a pressure of approximately 48 bar and well below the vapor pressure of the $CO_2$, the water-rich layer was approximately equal to the original volume of water added to the system. The acetone-rich layer increases in volume in excess of the original volume of acetone due to expansion by carbon dioxide.

The water rich layer was drained from the acetone rich layer. The addition of $CO_2$ below the vapor pressure enables the separation of the water from the acetone.

Example 5

Drying Onions

White onions were obtained from a local grocery, peeled of their outer skin, cut into 2 cm cubic portions, and further minced with a food processor. The resultant onion slurry was placed between a paper towel to remove excess fluid via absorbance. The solid was divided into 6 samples, each approximately 25 g and placed within 50 mL laboratory centrifuge tubes. To each tube was added 20 g of neat acetone. The tubes were placed in a centrifuged and processed at 3000 RPM (approximately 300 g) for 2 minutes. After centrifuging, the supernatant was decanted from the solid and collected. The resultant solids was combined with an additional 20 g of neat acetone, mixed well, centrifuged, and supernatant decanted and combined with the first stage's supernatant. A third stage identical to the first and second stage was performed.

The supernatant solution of acetone-water was placed in a 304 stainless steel pressure vessel with a pressure rating of 100 bar (1450 psi) and 180° C. The system was instrumented with a pressure gauge. The system was connected to a carbon dioxide cylinder with a vapor draw. $CO_2$ was introduced into the chamber in sufficient quantity to raise the system pressure to 50 bar. The drain line employed a sight glass with a 103 bar (1500 psi) pressure rating. The sight glass enabled observation of the liquid flowing from the chamber. The water was drained from the chamber using a needle valve. When the phase boundary was observed in the sight glass, the flow was discontinued. The liquid removed was water with less than 1 wt % acetone in solution. The acetone was stripped from the water by pumping air through a porous diffuser. The acetone was released from the chamber. For purposes of this experiment, the carbon dioxide was vented. The acetone could be recycled. The water was available for either reuse or disposal.

The slurry of insoluble onion solids, acetone, and water from the third stage concentrate was charged into the same pressure chamber as used above. The chamber was completely dried prior to charging with the onion solids. Liquid carbon dioxide equal to ten times the mass of the slurry charged into the chamber was flowed through the chamber from bottom to top and, subsequently, flashed to vapor. In this experiment, carbon dioxide was not recovered; although carbon dioxide recycling is well known in the art of supercritical fluid extraction. The liquid carbon dioxide was drained via the bottom valve in the chamber. The pressure was vented from the chamber. The dehydrated, insoluble onion solids were removed. This material has the same organoleptic profile as dried white onions. The material was measured via Karl Fischer and found to have a water content of 8 wt %.

Example 6

Separation of Vegetable Oil from Acetone Using Water (2 wt %)

Acetone (25.58 g) and vegetable oil (10.37 g) were mixed in a 50 ml graduated cylinder. The resulting single phase mixture was 71 wt % acetone and 29 wt % vegetable oil. A total of 0.73 g of water was added to the mixture resulting in clouding of the mixture. The cloudy nature of the mixture was due to precipitation of the vegetable oil from the acetone/vegetable oil mixture. After approximately 5 minutes, two distinct liquid layers had formed. The two phases were separated and weighed. The light phase was 22.32 g and the heavy phase was 12.94 g.

The concentration of oil contained within the heavy phase was determined by the amount of mass remaining after evaporation at 120° C. The oil content on the heavy phase was measured as 52 wt %. The total mass of oil in the heavy phase was 6.77 g which correlates to 65 wt % of the total oil in the starting mixture. By adding a small amount of water, the oil was concentrated from 29 wt % to 52 wt %.

TABLE 2

Summary for Separation of Vegetable Oil from Acetone Using Water (2 wt %)

| Component | Acetone | Vegetable oil | Water |
|---|---|---|---|
| Initial mixture, wt % | 71% | 29% | 0% |
| Mixture after water addition, wt % | 70% | 28% | 2% |
| Light phase*, wt % | NA | 16% | NA |
| Heavy phase, wt % | NA | 52% | NA |
| Concentration factor | NA | 1.8 | NA |
| Percent recovered in heavy phase*, wt % | NA | 65% | NA |

*Values calculated by mass balance

Example 7

Separation of Vegetable Oil from Acetone Using Water (22 wt %)

The above procedure was repeated using a mixture containing 16.24 g of acetone and 6.44 g of vegetable oil. The precipitation was performed using 6.37 g of water. The light phase had a mass of 20.52 g and the heavy phase had a mass of 7.90 g. The concentration of oil in the heavy phase was determined to be 83 wt %, for a total mass of 6.54 g of oil. For practical purposes, this is complete recovery of the oil from the starting mixture and a concentration of the oil by a factor of 2.9 from the starting mixture.

TABLE 3

Separation of Vegetable Oil from Acetone Using Water (22 wt %)

| Component | Acetone | Vegetable oil | Water |
|---|---|---|---|
| Initial mixture, wt % | 72% | 28% | 0% |
| Mixture after water addition, wt % | 56% | 22% | 22% |
| Light phase*, wt % | NA | 0% | NA |
| Heavy phase, wt % | NA | 83% | NA |
| Concentration factor | NA | 2.9 | NA |
| Percent recovered in heavy phase*, wt % | NA | 101% | NA |

*Values calculated by mass balance

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A process of recovering acetone from an aqueous solution comprising
    a) contacting an aqueous solution comprising at least about 40 wt % water and at least about 30 wt % acetone with vapor phase carbon dioxide in an amount that is about 10-50 wt/wt % of the aqueous solution, wherein the carbon dioxide disrupts the aqueous solution into a biphasic mixture comprising an acetone-rich phase and a water-rich phase; and
    b) non-thermally separating the acetone-rich phase from the water-rich phase, thereby recovering substantially all the acetone from the aqueous solution.

2. The process of claim 1, wherein the process is performed at ambient temperature.

3. The process of claim 1, wherein the process is performed at a temperature below 31° C.

4. The process of claim 1, wherein the process is performed at a pressure that is about 0.5 to about 0.95 the vapor pressure of carbon dioxide.

5. The process of claim 1, wherein the process is performed at a temperature above 31° C.

6. The process of claim 1, wherein the aqueous solution is contacted with the carbon dioxide in a countercurrent column.

7. The process of claim 1, wherein the aqueous solution is contacted with the carbon dioxide in a vessel.

8. The process of claim 1, wherein the acetone-rich phase is separated from the water-rich phase by decantation, centrifuging or cyclonic separation.

9. The process of claim 1, further comprising the step of removing carbon dioxide from the acetone-rich phase.

10. The process of claim 1, wherein the process is continuous.

11. The process of claim 1, wherein the process is carried out at a large scale.

12. The process of claim 1, wherein the process does not involve distillation.

13. A process of drying hydrated feedstock at ambient temperature, comprising the following ordered steps of:
   a) contacting the hydrated feedstock comprising water and insoluble solid with acetone, thereby yielding a first slurry comprised of at least about 30% acetone, water and the insoluble solid, wherein the acetone extracts the water from the insoluble solid;
   b) extracting the acetone and water from the insoluble solid by contacting with liquid phase carbon dioxide; thereby yielding a second slurry comprised of carbon dioxide, acetone, water and the insoluble solid, wherein the carbon dioxide displaces the water and acetone in the insoluble solid;
   c) separating the insoluble solid from the second slurry; thereby yielding insoluble solid saturated with liquid phase carbon dioxide and a solution comprising liquid phase carbon dioxide, acetone and water;
   d) depressurizing the insoluble solid to atmospheric pressure to release gas phase carbon dioxide, thereby yielding dried or dewatered insoluble solid;
   e) contacting the solution of step c) with vapor phase carbon dioxide, thereby splitting the solution into an upper acetone-rich phase and a lower water-rich phase; and
   f) non-thermally separating the upper acetone-rich phase from the lower water-rich phase.

14. The process of claim 13, wherein the hydrated feedstock further comprises oil, and the acetone is recovered by
   i) separating the insoluble solid from the first slurry, thereby yielding a solution comprising acetone, water and oil;
   ii) adding water to the solution comprising acetone, water and oil to form a biphasic mixture comprising an oil-rich phase and a water rich phase;
   iii) contacting the oil-rich phase with liquid phase carbon dioxide, thereby stripping the acetone from the oil; and
   iv) contacting the water-rich phase with vapor phase carbon dioxide, thereby splitting the solution into an upper acetone-rich phase and a lower water-rich phase; and
   v) non-thermally separating the upper acetone-rich phase from the lower water-rich phase.

15. The process of claim 13, further comprising the step of recovering the gas phase carbon dioxide released from the solution.

16. The process of claim 13, wherein the process is continuous.

17. The process of claim 13, wherein the process is carried out at a large scale.

18. The process of claim 13, wherein the process does not involve distillation.

19. The process of claim 13, wherein the feedstock is biological matter.

20. The process of claim 19, wherein the biological matter is plant matter.

21. The process of claim 19, wherein the biological matter is a single cell organism.

22. The process of claim 13, wherein the feedstock is hydrocarbon laden matter.

23. The process of claim 13, wherein the feedstock is geological matter.

24. The process of claim 13, wherein the feedstock is a wastewater stream.

25. A process of acetone-drying hydrated feedstock at ambient temperature, comprising:
   a) contacting the hydrated feedstock comprising water and insoluble solid with acetone, thereby yielding a first slurry comprised of acetone, water and the insoluble solid, wherein the acetone extracts the water from the insoluble solid;
   b) separating the insoluble solid within the first slurry; thereby yielding insoluble solid saturated with acetone and a first solution comprising acetone and water; wherein the insoluble solid is dehydrated, and
   c) recovering the acetone from the solution of step b) comprising contacting the solution with vapor phase carbon dioxide, thereby splitting the solution into an acetone-rich phase and a water-rich phase and separating the acetone-rich phase from the water-rich phase; wherein the acetone is recovered.

26. The process of claim 25, wherein the process is performed at ambient temperature.

27. The process of claim 25, wherein the process is continuous.

28. The process of claim 25, wherein the acetone-rich phase recovered in step c) is contacted with the hydrated feedstock in step a).

29. The process of claim 25, further comprising after step b) the steps of:
   i) extracting the acetone and water from the insoluble solid by contacting with liquid phase carbon dioxide; thereby yielding a second slurry comprised of carbon dioxide, acetone, water and insoluble solid, wherein the carbon dioxide displaces the water and acetone in the insoluble solid;
   ii) separating the insoluble solid from the second slurry; thereby yielding insoluble solid saturated with liquid phase carbon dioxide and a second solution comprising liquid phase carbon dioxide, acetone and water; and
   iii) depressurizing the insoluble solid saturated with liquid phase carbon dioxide to atmospheric pressure to release gas phase carbon dioxide, thereby yielding dehydrated insoluble solid.

30. The process of claim 29, wherein the gas phase carbon dioxide released is captured and pressurized to liquid phase and contacted with the first slurry of step a).

31. The process of claim 29, wherein the first solution and the second solution are combined before performing step c).

32. The process of claim 25, wherein the hydrated feedstock comprises oil, wherein the acetone extracts the water and the oil from the insoluble solid, yielding a first solution comprising acetone, water and oil; and further comprising after step b) the step of non-thermally separating the acetone from the oil.

33. The process of claim 32, wherein the acetone is separated from the oil by adding water to the first solution comprising acetone, water and oil to form a biphasic mixture comprising an oil-rich phase and a water rich phase; and contacting the oil-rich phase with liquid phase carbon dioxide, thereby stripping the acetone from the oil; and contacting the water-rich phase with vapor phase carbon dioxide as in step c).

34. The process of claim 25, wherein the process is carried out at a large scale.

35. The process of claim 25, wherein the process does not involve distillation.

36. The process of claim 25, wherein the feedstock is biological matter.

37. The process of claim 36, wherein the biological matter is plant matter.

38. The process of claim 36, wherein the biological matter is a single cell organism.

39. The process of claim 25, wherein the feedstock is hydrocarbon laden matter.

40. The process of claim 25, wherein the feedstock is geological matter.

41. The process of claim 25, wherein the feedstock is a wastewater stream.

42. The process of claim 13, wherein the process is performed at ambient temperature and a pressure that is about 0.5 to about 0.95 the vapor pressure of carbon dioxide.

43. The process of claim 25, wherein the process is performed at ambient temperature and a pressure that is about 0.5 to about 0.95 the vapor pressure of carbon dioxide.

* * * * *